US008586527B2

(12) United States Patent
Singh

(10) Patent No.: US 8,586,527 B2
(45) Date of Patent: Nov. 19, 2013

(54) CERIVASTATIN TO TREAT PULMONARY DISORDERS

(75) Inventor: Jaipal Singh, Atlanta, GA (US)

(73) Assignee: Jaipal Singh, Carmel, IN (US)

( * ) Notice: Subject to any disclaimer, the term of this patent is extended or adjusted under 35 U.S.C. 154(b) by 0 days.

(21) Appl. No.: 13/277,853

(22) Filed: Oct. 20, 2011

(65) Prior Publication Data

US 2013/0098357 A1 Apr. 25, 2013

(51) Int. Cl.
*A61K 31/00* (2006.01)
(52) U.S. Cl.
USPC ................ 514/1.1; 514/15.7; 514/79; 514/89
(58) Field of Classification Search
USPC .......................................................... 514/1.1
See application file for complete search history.

(56) References Cited

U.S. PATENT DOCUMENTS

| | | | |
|---|---|---|---|
| 4,765,539 A | 8/1988 | Noakes | |
| 4,897,355 A | 1/1990 | Eppstein | |
| 4,938,763 A | 7/1990 | Dunn | |
| 4,962,885 A | 10/1990 | Coffee | |
| 5,006,530 A | 4/1991 | Angerbauer | |
| 5,177,080 A | 1/1993 | Angerbauer | |
| 5,411,737 A | 5/1995 | Hsu | |
| 5,480,656 A | 1/1996 | Okada | |
| 6,113,943 A | 9/2000 | Okada | |
| 6,147,109 A | 11/2000 | Liao et al. | |
| 6,361,792 B1 | 3/2002 | Long, Jr. | |
| 6,589,549 B2 | 7/2003 | Shih | |
| 7,052,678 B2 | 5/2006 | Vanbever | |
| 7,550,155 B2 | 6/2009 | Zhang | |
| 7,569,557 B2 | 8/2009 | Backensfeld | |
| 2001/0006656 A1 | 7/2001 | Harlan et al. | |
| 2005/0038102 A1 | 2/2005 | Liao et al. | |
| 2006/0058262 A1 | 3/2006 | Zoppetti | |
| 2006/0067952 A1 | 3/2006 | Chen | |
| 2007/0207173 A1 | 9/2007 | Chen | |
| 2009/0325958 A1 | 12/2009 | Navratil | |
| 2010/0010024 A1* | 1/2010 | Von Nussbaum et al. | 514/274 |
| 2010/0295113 A1 | 11/2010 | Kang | |
| 2011/0015266 A1 | 1/2011 | Hanefeld | |
| 2011/0045050 A1 | 2/2011 | Elbayoumi | |

OTHER PUBLICATIONS

Urakami et al., The American Journal of Pathology (Jun. 2011) vol. 178, No. 6, pp. 2489-2495.*
Heffernan et al., Bioconjugate Chem. (2005), 16, 1340-1342.*
Pullamsetti et al., The FASEB Journal (2005), 19, 1175-1177.*
Sanchez et al., American Journal of Respiratory and Critical Care Medicine (2007) vol. 176, No. 10, 1041-1047.*
Almarsson and Zaworotko, "Crystal engineering of the composition of pharmaceutical phases. Do pharmaceutical co-crystals represent a new path to improved medicines" , Chem. Commun., 17:1889-96 (2004).
Boger, "Asymmetric dimethylarginine (ADMA) and cardiovascular disease: insights from prospective clinical trials" , Vasc. Med., 10:S19-S25 (2005).
Brigham, et al., "Expression of a prokaryotic gene in cultured lung endothelial cells after lipofection with a plasmid vector" , Am J. Resp Cell. Mol. Biol.,195-100 (1989).
Cao, et al., "Lung-targeted delivery system of curcumin loaded gelatin microspheres" , Drug Deliv. 18(8):545-54. (2011).
Cao, et al., "Preparation and characterization of curcumin loaded gelatin microspheres for lung targeting" , Zhonq Yao Cai ,32(3):423-6 (2009). Article in Chinese with English translation.
Carvalho, et al., "Formulations for pulmonary administration of anti-cancer agents to treat lung malignancies" , J. Aerosol Med Pulm Drug Deliv., 24(2):61-80 (2011).
Cortesi, et al., "Sugar cross-linked gelatin for controlled release: microspheres and disks" , Biomaterials, 19:1641-49 (1998).
Craparo, et al., "Phospholipid-polyaspartamide micelles for pulmonary delivery of corticosteroids" , Int J. Pharm., 406(1-2):135-44 (2011).
Dandekar, et al., "Pulmonary targeting of nanoparticle drug matrices" , J. Aerosol Med. Pulm Deliv., 23(6):343-53 (2010).
Dolovich, et al., "Aerosol drug delivery: developments in device design and clinical use" , Lancet ,377(9770):1032-45 (2011).
Feigner, et al., "Lipofection: a highly efficient, lipid-mediated DNA-transfection procedure" , PNAS, 84:7413-71(987).
Forbes, et al., "Challenges in inhaled product development and opportunities for open innovation" , Adv Drug Deliv Rev., 63(1-2):69-87 (2011).
Gentile, et al., "New asthma drugs: small molecule inhaled corticosteroids" , Curr Opin Pharmacol, 10(3):260-5 (2010).
Gill, et al., "Paclitaxel loaded PEG(5000)-DSPE micelles as pulmonary delivery platform: formulation characterization, tissue distribution, plasma pharmacokinetics, and toxicological evaluation", Eur. J. Pharm Biopharm, 79(2):276-84 (2011).
Gupta, et al., "PLGA microparticles encapsulating prostaglandin E1-hydroxypropyl-$^2$-cyclodextrin (PGE1-HP$^2$CD) complex for the treatment of pulmonary arterial hypertension (PAH)" , Pharm. Res., 28(7)1733-49 (2011).
Gupta, et al., "Inhalational therapy for pulmonary arterial hypertension: current status and future prospects" , Crit. Rev. Ther. Drug Carrier Syst, 27(4):313-70 (2010).
Haleblian, "Characterization of habits and crystalline modification of solids and their pharmaceutical applications" , J. Pharm. Sci., 64(8):1269-88 (1975).
Humbert, et al.,"Cellular and molecular pathobiology of pulmonary arterial hypertension" , J. Am. Coll. Cardiol. 43(12):13S-24S (2004).
Humbert, et al., "Increased interleukin-1 and interleukin-6 serum concentrations in severe primary pulmonary hypertension" , Am. J. Resp. Crit. Care Med., 151:1628-1631 (1995).

(Continued)

*Primary Examiner* — Karlheinz R Skowronek
*Assistant Examiner* — Catherine Mader

(57) ABSTRACT

Pharmaceutical formulations and methods of using thereof for the treatment and prevention of pulmonary arterial hypertension are provided. The formulations contain one or more agents to simultaneously reduce ADMA levels in a patient and reduce inflammatory processes in the pulmonary vasculature of a patient. The formulations contain a therapeutically effective amount of cerivastatin, a cerivastatin analog, or a pharmaceutically acceptable salt, prodrug, clathrate, or solvate thereof in a carrier suitable for pulmonary administration.

19 Claims, 6 Drawing Sheets

(56) References Cited

OTHER PUBLICATIONS

Jain, et al., "Lactose-Conjugated PLGA Nanoparticles for Enhanced Delivery of Rifampicin to the Lung for Effective Treatment of Pulmonary Tuberculosis", PDA J. Pharm Sci Technol., 64(3):278-87 (2010).
Katsiki, et al., "Pulmonary arterial hypertension and statins: an update", Curr. Opin. Cardiol., 26:322-326 (2011).
Kawaguchi, et al., "Phagocytosis of latex particles by leucocytes. I. Dependence of phagocytosis on the size and surface potential of particles", Biomaterials ,7: 61-66 (1986).
Krenis and Strauss, "Effect of size and concentration of latex particles on respiration of human blood leucocytes", Proc. Soc. Exp. Med., 107:748-750 (1961).
Kurmi, et al., "Micro- and nanocarrier-mediated lung targeting", Expert Opin Drug Deliv., 7(7):781-94 (2010).
Okamoto, et al., "Chitosan-interferon-$^2$ gene complex powder for inhalation treatment of lung metastasis in mice", J. Control, Release, 150(2):187-95 (2011).
Pourshahab, et al., "Preparation and characterization of spray dried inhalable powders containing chitosan nanoparticies for pulmonary delivery of isoniazid", J. Microencapsulation, 28(7):605-13 (2011).
Pullamsetti, et al., "Increased levels and reduced catabolism of asymmetric and symmetric dimethylarginines in pulmonary hypertension", FASEB J., 19 (9):1175-77 (2005).
Rakotoniaina, et al., "The protective effect of HMG-CoA reductase inhibitors against monocrotaline-induced pulmonary hypertension in the rat might not be a class effect: comparison of pravastatin and atorvastatin" ,Naunyn Schmiedobergs Arch Pharmacol., 374(3)195-206 (2006).
Rubin, "Pulmonary arterial hypertension", Proc. Am. Thorac. Soc., 3:111-115 (2006).
Rudt and Muller, "In vitro phagocytosis assay of nano" and microparticles by chemiluminescence: I. Effect of analytical parameters, particle, Journal of Controlled Release, 22 ( 1992 ) 263-272.
Salem, "Sustained-release progesterone nanosuspension following intramuscular injection in ovariectomized rats" , Int J Nanomedicine., 5:943-54 (2010).
Schleh, et al., "The influence of pulmonary surfactant on nanoparticulate drug delivery systems", Eur J. Pharm Biopharm., 77(3):350-2 (2011).
Simonneau, et al., "Clinical classification of pulmonary hypertension", J. Am. Coll. Cardio,. 43(12) Suppl. S: 5S-12S (2004).
Skoro-Sajer, et al. "Asymmetric dimethylarginine is increased in chronic thromboembolic pulmonary hypertension", Am. J. Resp. Crit. Care Med.,176:1154-60 (2007).
Tuder, et al., "Exuberant endothelial cell growth and elements of inflammation are present in plexiform lesions of pulmonary hypertension", Am. J. Pathol., 144: 275-285 (1994).
Urakami, et al., "Peptide-directed highly selective targeting of pulmonary arterial hypertension", Am. J. Pathol., 178(6):2489-2495 (2011).
Weitzenblum, "Chronic cor pulmonale", E. Heart , 89: 225-230 (2003).
Zhang, et al., "Lipid nanoemulsions loaded with doxorubicin-oleic acid ionic complex: characterization, in vitro and in vivo studies", Pharmazie, 66(7):496-505 (2011).
Barreto et al., "Rosuvastatin and vascular dysfunction markers in pulmonary arterial hypertension: a placebo-controlled study" *Brazilian J Med Res* 41(8): 657-663 (2008).
Chen et al., "Nanoparticle-mediated delivery of pitavastatin into lungs ameliorates the development and induces regression of monocrotaline-induced pulmonary artery hypertension" *Hypertension*, 57:343-350 (2011).
Furberg and Pitt, "Withdrawal of cerivastatin from the world market" *Curr Control Trials Cardiovasc Med* 2:205-207 (2001).
Kawut et al., "Randomized Clinical Trial of Aspirin and Simvastatin for Pulmonary Arterial Hypertension: ASA-STAT" *Circulation* 123: 2985-2993 (2011).
McMurtry et al., "Statin therapy, alone or with rapamycin, does not reverse monocrotaline pulmonary arterial hypertension: the rapamcyin-atorvastatin-simvastatin study" *Am. J. Physiol. Lung Cell Mol. Physiol.* 293(4):L933-L940 (2007).
Rakotoniaina et al., "The protective effect of HMG-CoA reductase inhibitors against monocrotaline-induced pulmonary hypertyension in the rat might not be a class effect: comparison of pravastatin and atorvastatin" *Naunyn-Schmiedeberg's Arch Pharmacol* 374: 195-206 (2006).
Zeng et al., "Atorvastatin in Pulmonary Hypertension (APATH) Study" *Eur Respir J.* 40(1): 67-74 (2012).

* cited by examiner

CERIVASTATIN TO TREAT PULMONARY DISORDERS

FIELD OF THE INVENTION

The present invention relates to the use of cerivastatin formulations for the prevention and treatment of pulmonary disorders, including pulmonary arterial hypertension (PAH).

BACKGROUND OF THE INVENTION

Pulmonary arterial hypertension (PAH) is a rare but devastating disorder of the pulmonary circulation affecting 50,000 to 100,000 persons in the United States. Pulmonary diseases, such as pulmonary hypertension (PH), can be life threatening. Pulmonary hypertension is a broad clinical term used to describe pulmonary conditions which involve an increase in blood pressure in the lung vasculature (i.e., the pulmonary artery, the pulmonary vein, or the pulmonary capillaries). The increase in blood pressure leads to shortness of breath, dizziness, fainting, and other symptoms, all of which are exacerbated by exertion. Eventually, PH can lead to chronic hypoxia, heart failure, and death.

According to current clinical classification, pulmonary hypertension is divided into five different categories based on pathophysiological mechanisms, clinical presentation, and therapeutic methods. See Simonneau, et al. J. Am. Coll. Cardio. 43(12) Suppl. S: 5S-12S (2004). The five different types of PH include (1) pulmonary arterial hypertension (PAH); (2) PH with left heart disease (i.e., pulmonary venous hypertension); (3) PH associated with lung diseases and/or hypoxemia (4) PH due to chronic thrombotic and/or embolic disease; and (5) miscellaneous pulmonary hypertension.

Pulmonary arterial hypertension (PAH) is a form of pulmonary hypertension characterized by elevated blood pressure in the arteries of the lungs. Arterial blood pressure becomes elevated when the arterioles within the lung become narrowed, resulting in increased pulmonary vascular resistance and remodeling of distal pulmonary arteries. Eventually, the increased workload of the heart causes right ventricular hypertrophy (a condition known as cor pulmonale). Furthermore, as blood flow through the lungs decreases, the left side of the heart receives less blood. Therefore, the left side of the heart also struggles to pump a sufficient supply of oxygen to the rest of the body, especially during physical activity. Without treatment, pulmonary arterial hypertension leads to congestive heart failure and death.

The pulmonary vascular injury underlying PAH can occur in an idiopathic form (IPAH) or can be associated with an underlying risk factor or condition. PAH has been associated with many disease states, including congenital heart disease, HIV infection, lupus, or chronic obstructive pulmonary disease (COPD), sickle cell disease, scleroderma, rheumatoid arthritis, portal hypertension. However, it is now recognized that pulmonary arterial obstruction by vascular proliferation and remodeling is the hallmark of PAH pathogenesis. Humbert, et al. J. Am. Coll. Cardiol. 43(13): S-24S (2004); Rubin Proc. Am. Thorn. Soc. 3:111-115 (2006).

Because the five types of PH involve different pathophysiological mechanisms, treatments methods will vary depending on whether the PH is arterial, venous, hypoxic, thromboembolic, or miscellaneous. For example, PAH involves the vasoconstriction or tightening of blood vessels connected to and within the lungs. As a result, pulmonary arterial hypertension is currently treated by the administration of calcium channel antagonists, prostacyclins, endothelin receptor antagonists, and anticoagulants. In contrast, pulmonary venous hypertension does not involve obstruction of blood flow in the lungs. Rather, the left heart fails to pump blood efficiently, leading to pulmonary edema and pleural effusions. As a result, treatment methods, which include the administration of diuretics, beta blockers, ACE inhibitors, as well as surgical intervention to repair/replace the mitral valve or aortic valve, strive to improve left ventricular function.

It is hoped that by understanding the mechanisms responsible for the pulmonary vascular remodeling in PAH, effective therapeutic strategies for treating or preventing PAH can be developed. In PAH, the process of pulmonary vascular remodeling involves all layers of the vessel wall. However, endothelial dysfunction attributable to the reduced bioavailability of vasodilators such as nitric oxide (NO) has been shown to play an important role in the pathogenesis of PAH. Skoro-Sajer, et al. Am. J. Resp. Crit. Care Med. 176:1154-1160 (2007).

NO is biosynthesized by nitric oxide synthases (NOS), which convert L-arginine to L-citrulline, releasing nitric oxide. Asymmetric dimethylarginine (ADMA) is an endogenous inhibitor of nitric oxide synthase (NOS), and elevated levels of ADMA have been observed in patients suffering from PAH. Pullamsetti, S., et al. FASEB J. 19(9): 1175-1177 (2005). Elevated ADMA levels have also been linked to numerous clinical conditions, including hypercholesterolemia, atherosclerosis, hypertension, chronic renal failure, chronic heart failure. Böger, R. H. Vase. Med. 10:S19-S25 (2005).

ADMA levels in vivo are regulated by dimethylarginine dimethylaminohydrolase (DDAH), which metabolizes ADMA. The enzyme DDAH2 represents the predominant endothelial DDAH isoform. In patients suffering from pulmonary arterial hypertension, the expression of DDAH2 is reduced at both the mRNA and the protein level. Pullamsetti, S., et al. FASEB J. 19(9): 1175-1177 (2005). These findings suggest that the suppression of endothelial DDAH2 expression and function represents an important underlying mechanism for the pulmonary vascular remodeling in PAH.

Other factors, including inflammatory pathways, are also known to contribute to pulmonary vascular remodeling in PAH. Perivascular inflammatory cell infiltrates composed chiefly of monocytes and macrophages have been found in the lung tissue of patients afflicted with pulmonary arterial hypertension. Tuder, R. M. et al. Am. J. Pathol. 144: 275-285 (1994). Patients with PAH have also been shown to exhibit higher circulating levels and pulmonary expression of inflammatory cytokines and chemokines. Humbert, M., et al. Am. J. Resp. Crit. Care Med. 151:1628-1631 (1995).

The chemokine receptor CCR2 is known to play a central role in the establishment and maintenance of chronic inflammatory processes. CCR2 and its ligands (such CC chemokine ligand 2 (CCL2), also known as macrophage chemoattractant protein-1 (MCP-1)) represent a critical signaling pathway responsible for the recruitment of peripheral blood monocytes to locations of immune-mediated inflammation. Once recruited, these monocytes become inflammatory macrophages which function to establish and maintain a chronic inflammatory state. Studies have demonstrated that CCR2 is overexpressed in the pulmonary endothelial cells and pulmonary-artery smooth muscle cells of patients suffering from pulmonary arterial hypertension, resulting in a chronic inflammatory response in the pulmonary arteries. These findings suggest that the inflammatory response triggered by CCR2 overexpression in pulmonary endothelial cells and pulmonary-artery smooth muscle cells represents another important underlying mechanism for the pulmonary vascular remodeling in PAH.

Current therapies for pulmonary arterial hypertension, including calcium channel antagonists, prostacyclins, endothelin receptor antagonists, and anticoagulants, are unsatisfactory. Each of these treatment methods possesses significant clinical limitations and/or side effects. See Gupta, et al., Crit. Rev. Ther. Drug Carrier Syst 27(4):313-70 (2010). A major shortcoming of anti-PAH medications is their short half-lives, requiring them to be administered via parenteral routes, which lead to undesirable side effects, including systemic vasodilation. Inhalational delivery of anti-PAH drugs provides an attractive alternative to conventional routes, with ease of administration and minimal systemic vasodilation. Recently, the U.S. Food and Drug Administration approved inhalable iloprost (Ventavis®), a prostacyclin analogue, for PAH treatment. Other drugs being studied for their potential in inhalable PAH therapy include PGE1, treprostinil, vasoactive intestinal peptide, and fasudil. Controlled-release inhalable delivery systems for anti-PAH medications have also been proposed to facilitate long-term and selective vasodilation of pulmonary arteries.

Preliminary testing using statins has indicated the potential for benefit, but results have been inconsistent. See Katsiki, et al. Curr. Opin. Cardiol. 26:322-326 (2011); Naunyn Schmiedobergs Arch Pharmacol. 374(3):195206 (2006) reported that pravastatin but not atorvastatin improved pulmonary aterial hypertension when injected intraperitoneally.

Despite these treatments, the average life expectancy of a PAH patient is generally under five years from the diagnosis of the disease. United States Patent Application No. US20090325958 to Navratil, et al. Therefore, there is a long felt need for improved therapies for pulmonary arterial hypertension.

Therefore, it is an object of the invention to provide methods of treating or preventing diseases associated with high ADMA levels, including pulmonary arterial hypertension.

It is also an object of the invention to provide methods of selectively inducing DDAH2 activity to treat or prevent pulmonary arterial hypertension.

It is a further object of the invention to provide methods of inhibiting CCR2 gene expression to treat or prevent pulmonary arterial hypertension.

It is further object of the invention to improve endothelial function by inducing KLF2.

SUMMARY OF THE INVENTION

Pharmaceutical formulations containing an effective amount of cerivastatin, an analog of cerivastatin, or a pharmaceutically acceptable prodrug, salt, solvate, or clathrate thereof to treat or prevent pulmonary arterial hypertension (PAH) in combination with a pharmaceutically acceptable carrier have been developed. Preferably, the formulations are suitable for pulmonary administration of the active agents. The pharmaceutical formulations contain one or more active agents which can simultaneously induce DDAH2 activity in the pulmonary endothelial cells of a patient with elevated levels of ADMA, and reduce CCR2 expression in the pulmonary endothelial cells of a patient. By inducing DDAH2 activity, AMDA levels are reduced, resulting in an increase in levels of the vasodilator nitric oxide in the pulmonary vasculature. By reducing CCR2 expression in the lung of a patient, the inflammatory processes in the pulmonary vasculature related to the pulmonary vascular remodeling in PAH are slowed.

By administering the pharmaceutical formulation locally to the lungs of a patient, low dosage of the pharmaceutical formulation can provide therapeutic benefit. This minimizes the risk of side effects associated with the systemic administration of cerivastatin. In some embodiments, cerivastatin, an analog of cerivastatin, or a pharmaceutically acceptable prodrug, salt, solvate, or clathrate thereof is administered at dosage of less than 0.1 mg/kg per day, more preferably at a dosage of less than 0.03 mg/kg per day, most preferably at a dosage of less than 0.001 mg/kg per day.

In some cases, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension that is not linked to any apparent risk factor or condition. In some cases, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension that is inherited (i.e., genetically based). In some cases, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension that is associated with one or more risk factors or associated diseases or disorders.

Pulmonary administration of the pharmaceutical formulations will preferably provide at least one beneficial clinical result, including, but are not limited to, the lessening or prevention of pulmonary arterial hypertension, alleviation of one or more symptoms of pulmonary arterial hypertension, decreased resting mean pulmonary arterial pressure (mPAP), decreased right ventricular (RV) wall thickness, increased pulmonary artery acceleration time (PAAT), diminishment of extent of pulmonary artery hypertension, stabilized (i.e., not worsening) state of pulmonary artery hypertension, delayed disease progression, amelioration or palliation of the disease state, and remission (whether partial or total). Treatment can also include prolonging survival as compared to expected survival if not receiving treatment.

BRIEF DESCRIPTION OF THE DRAWINGS

FIG. 1A shows that cerivastatin has a relatively small and non-concentration dependent effect on the expression of DDAH1 in endothelial cells, while FIG. 1B shows that cerivastatin has a significant (more than 600%) and dose dependent effect on the expression of DDAH2.

FIGS. 2A and 2B plot the relative KLF2 and CCR2 mRNA levels upon administration of tumor necrosis factor alpha (TNF-α), TNF-α+10 μM cerivastatin, TNF-α+10 μM simvastatin, TNF-α+10 μM lovastatin, TNF-α+10 μM atorvastatin.

FIG. 5A shows actual RV cavity thickness (cm) measurements. FIG. 5B shows RV thickness as percent change relative to the control.

FIG. 7B shows that injection of MCT (simulating PAH) resulted in a decrease in PAAT to 40.5% of the control. Intratracheal injection of cerivastatin resulted in a statistically significant increase in PAAT to 60.7% of the control.

DETAILED DESCRIPTION OF THE INVENTION

Figure 1A:
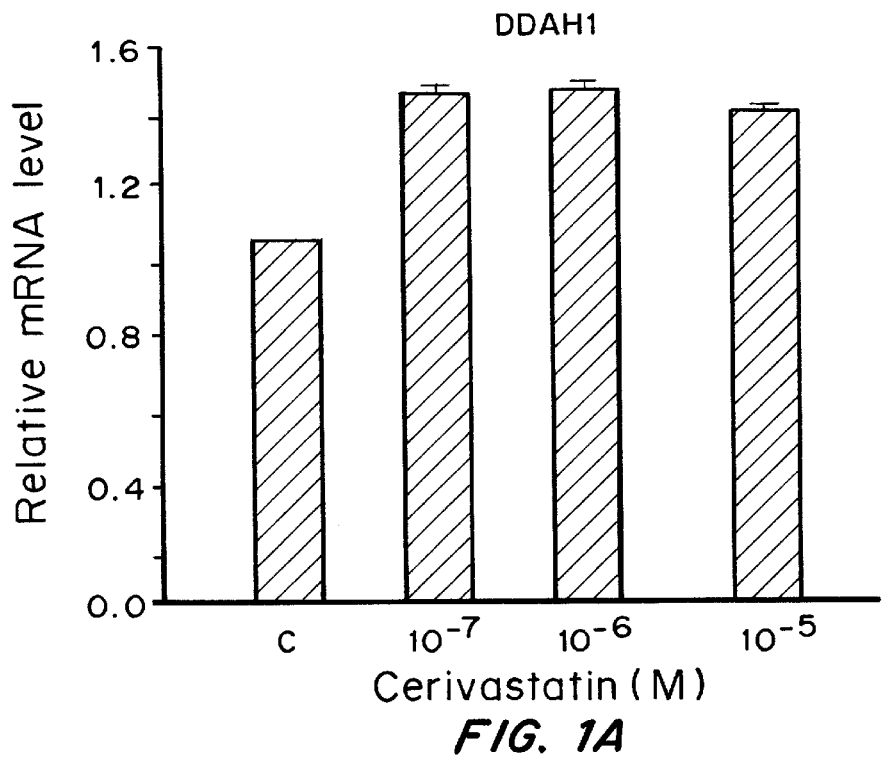
FIGS. 1A and 1B shows the effect of cerivastatin on the expression of DDAH1 (FIG. 1A) and DDAH2 (FIG. 1B) in endothelial cells. In both cases, the relative mRNA level is plotted as a function of cerivastatin concentration (mol/L). Cerivastatin selectively induces DDAH2 gene expression in human endothelial cells.

It has been discovered that cerivastatin is effective to treat PAH. Other statins that have been tested for efficacy in treatment of PAH have not been effective. In some cases, even though the statin reduced RV thickening and vascular biology, they did not reduce PAH. The mean pulmonary artery pressure is an important clinical endpoint for PAH disease states. Cerivastatin significantly lowered pulmonary arterial pressure. Cerivastatin is believed to also be effective to reverse or regress the disease state, since it induces DDAH2, reduces CCR2, and inhibits smooth muscle cell proliferation. Direct delivery to the lung provides safer delivery while maintaining efficacy. Selective induction of DDAH2 as compared to DDAH1 was unexpected. DDAH2 is predominantly reduced in human disease. Therefore cerivastatin provides additional benefit in disease treatment by virtue of its effect on DDAH2, CCR2 and KLF2.

I. Definitions

"Cerivastatin", as used herein, refers to (3R,5S,6E)-7-[4-(4-fluorophenyl)-5-(methoxymethyl)-2,6-bis(propan-2-yl) pyridin-3-yl]-3,5-dihydroxyhept-6-enoic acid, the structure of which is shown below.

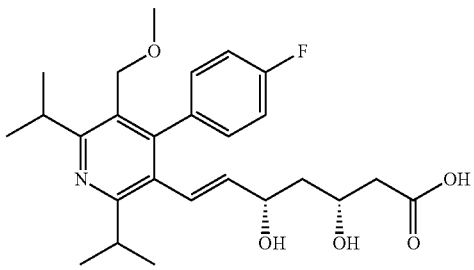 [SMILES: COCc1c(C(C)C)nc(C(C)C)c(/C=C/[C@@H](O)C[C@@H](O)CC(=O)O)c1-c1ccc(F)cc1]

"Pulmonary Hypertension", as used herein, refers to pulmonary conditions which involve an increase in blood pressure in the lung vasculature. Clinically, pulmonary hypertension can be classified as one of five different conditions: (1) pulmonary arterial hypertension (PAH); (2) PH with left heart disease; (3) PH associated with lung diseases and/or hypoxemia (4) PH due to chronic thrombotic and/or embolic disease; and (5) miscellaneous pulmonary hypertension. See Simonneau, et al. J. Am. Coll. Cardio. 43(12) Suppl. 5: 5S-12S (2004).

"Pulmonary Arterial Hypertension", as used herein, refers to a form of pulmonary hypertension characterized by elevated blood pressure in the arteries of the lungs. Human PAH is defined by a resting mean pulmonary arterial pressure (mPAP) of greater than 20 mmHg. Weitzenblum, E. Heart 89: 225-230(2003). Patients suffering from PAH also exhibit increased pulmonary vascular resistance (PVR; typically greater than 3 Wood units (240 dyn·s·cm$^{-5}$ or 2.4 mN·s·cm$^{-5}$)) in combination with normal pulmonary artery occlusion pressure (PAOP, also called pulmonary wedge pressure or PWP, or pulmonary capillary wedge pressure or PCWP; typically less than 15 mmHg). Pulmonary arterial obstruction by vascular proliferation and remodeling is the hallmark of PAH pathogenesis. The pulmonary vascular injury underlying PAH can occur in an idiopathic form (IPAH) or can be associated with an underlying risk factor or condition. PAH can be associated with many disease states, including congenital heart disease, HIV infection, lupus, or chronic obstructive pulmonary disease (COPD).

"Pulmonary administration", as used herein, refers to administration of a pharmaceutical formulation containing an active agent into the lungs by inhalation. As used herein, the term "inhalation" refers to intake of air to the alveoli. The intake of air can occur through the mouth or nose. The intake of air can occur by self-administration of a formulation while inhaling, or by administration via a respirator to a patient on a respirator.

"Inhalation Device", as used herein, refers to a device which facilitates delivery of an active agent via inhalation. Inhalation devices include, but are not limited to, dry powder inhalers, pressurized metered dose inhalers, breath actuated pressurized metered dose inhalers, nebulizers including vibrating mesh, ultrasonic and jet nebulizers, and soft mist inhalers.

"Pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

"Mass Median Aerodynamic Diameter" (MMAD), as used herein, refers to the median aerodynamic size of a plurality of particles. The "aerodynamic diameter" is the diameter of a unit density sphere having the same settling velocity, generally in air, as a powder and is therefore a useful way to characterize an aerosolized powder or other dispersed particle or particle formulation in terms of its settling behavior. The aerodynamic diameter encompasses particle or particle shape, density, and physical size of the particle or particle. MMAD can be experimentally determined by methods known in the art, such as by cascade impaction.

"Tap Density", as used herein, refers to a measure of the density of a powder. Tap density can be determined using the method of USP Bulk Density and Tapped Density, United States Pharmacopia convention, Rockville, Md., 10th Supplement, 4950-4951, 1999. Features which can contribute to low tap density include irregular surface texture and porous structure.

"Monodisperse" and "homogeneous size distribution", are used interchangeably herein and describe a plurality of nanoparticles or microparticles where the particles are the same or nearly aerodynamic diameter. As used herein, a monodisperse distribution refers to particle distributions in which 90% of the distribution lies within 5% of the mass median aerodynamic diameter.

"Co-administration", as used herein, refers to simultaneous and sequential administration of two or more different active agents. The two or more active agents can be included in the same or different pharmaceutical formulation. The two or more active agents can be intended to achieve the same or different clinical benefit. An appropriate time course for sequential administration may be chosen by the physician, according to such factors as the nature of a patient's illness, and the patient's condition.

"Acute administration", as used herein, refers to administration of a pharmaceutical formulation over a short period of time, to deliver a therapeutically effective amount of cerivastatin, an analog of cerivastatin, or a pharmaceutically acceptable prodrug, salt, solvate, or clathrate thereof in a small number of dose administrations, such as, for example, a single dose.

II. Pharmaceutical Formulations

Formulations are provided containing an effective amount of cerivastatin, an analog of cerivastatin, or a pharmaceutically acceptable prodrug, salt, solvate, or clathrate thereof to treat or prevent pulmonary arterial hypertension in combination with a pharmaceutically acceptable carrier.

The pharmaceutically acceptable carrier includes all components (i.e., excipients and/or additives) present in the pharmaceutical formulation other than the active agent or agents. The pharmaceutical carrier is composed of materials that are considered safe and effective and may be administered to an individual without causing undesirable biological side effects or unwanted interactions.

A. Active Agents

1. Cerivastatin

Formulations are provided that contain a therapeutically effective amount of cerivastatin, an analog of cerivastatin, or a pharmaceutically acceptable prodrug, salt, solvate, or clathrate thereof to treat or prevent pulmonary arterial hypertension.

In preferred embodiments, the formulation contains an effective amount of cerivastatin ((3R,5S,6E)-7-[4-(4-fluorophenyl)-5-(methoxymethyl)-2,6-bis(propan-2-yl)pyridin-3-yl]-3,5-dihydroxyhept-6-enoic acid) to treat or prevent PAH.

Formulations can also contain an analog of cerivastatin. Analogs of cerivastatin include structurally related compounds which display similar pharmacological activity when administered to a patient in need thereof. Suitable analogs include substituted 2,6-dialkyl-4-aryl-pyridines, such as those described in U.S. Pat. Nos. 5,006,530 and 5,117,080 to Angerbauer, et al., which are incorporated herein by reference.

Formulations can also contain a pharmaceutically acceptable prodrug of cerivastatin or a cerivastatin analog. Prodrugs of cerivastatin and cerivastatin analogs are compounds that, when metabolized in vivo, undergo conversion to compounds having the desired pharmacological activity. Prodrugs can be prepared by replacing appropriate functionalities present in cerivastatin or cerivastatin analogs with "pro-moieties" as described, for example, in H. Bundgaar, Design of Prodrugs (1985). Examples of prodrugs include ester, ether or amide derivatives of the compounds herein, and their pharmaceutically acceptable salts. For further discussions of prodrugs, see, for example, T. Higuchi and V. Stella "Pro-drugs as Novel Delivery Systems," ACS Symposium Series 14 (1975) and E. B. Roche ed., Bioreversible Carriers in Drug Design (1987).

Formulations can contain a pharmaceutically acceptable salt of cerivastatin or a cerivastatin analog. In some cases, it may be desirable to prepare a formulation containing a salt of cerivastatin or a cerivastatin analog due to one or more of the salt's advantageous physical properties, such as enhanced stability or a desirable solubility or dissolution profile.

Generally, pharmaceutically acceptable salts of cerivastatin and cerivastatin analogs can be prepared by reaction of the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found, for example, in Remington's Pharmaceutical Sciences, 20th ed., Lippincott Williams & Wilkins, Baltimore, Md., 2000, p. 704.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids.

Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate(pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

In some cases, the pharmaceutically acceptable salt of cerivastatin or a cerivastatin analog may include alkali metal salts, including but not limited to sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$)

halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

Formulations can also contain a pharmaceutically acceptable solvate of cerivastatin or a cerivastatin analog. Solvates of cerivastatin and cerivastatin analogs include molecular complexes formed between cerivastatin or a cerivastatin analog and one or more pharmaceutically acceptable solvent molecules (e.g., ethanol). The term "hydrate" refers to solvates in which the pharmaceutically acceptable solvent is water. A currently accepted classification system for solvates of organic compounds is one that distinguishes between isolated site, channel, and metal-ion coordinated solvates and hydrates. See, for example, K. R. Morris (H. G. Brittain ed.) *Polymorphism in Pharmaceutical Solids*, Marcel Dekker Inc., New York, N.Y. (1995), Isolated site solvates are solvates in which the solvent molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent is tightly bound, the solvate will have a well-defined stoichiometry independent of ambient humidity. However, when the solvent is weakly bound, as in channel solvates and in hygroscopic compounds, the solvent content will depend on humidity and drying conditions. In such cases, the solvate will generally incorporate solvent molecules in a non-stoichiometric ratio.

Formulations can also contain a pharmaceutically acceptable clathrate of cerivastatin or a cerivastatin analog. Clathrates are drug-host inclusion complexes formed when a drug is associated with or in a host molecule or molecules in stoichiometric ratio. For example, cerivastatin or cerivastatin analogs can form inclusion complexes with cyclodextrins or other host molecules.

Formulations can also contain pharmaceutically acceptable co-crystals of cerivastatin or a cerivastatin analog. Co-crystals are crystalline complexes of two or more molecular constituents, one of which is cerivastatin or a cerivastatin analog. The molecular constituents may be two or more neutral molecules, two or more salts, or a complex containing one or more neutral molecules and one or more salts. Co-crystals may be prepared by melt crystallization, recrystallization from solvents, or by physically mixing the components together, for example, by grinding. See, e.g., O. Almarsson and M. J. Zaworotko, Chem. Commun., 17:1889-1896 (2004). Examples of multi-component complexes are well known in the art. See, for example, J. K. Haleblian, J. Pharm. Sci. 64(8):1269-88 (1975).

Cerivastatin, analogs of cerivastatin, as well as pharmaceutically acceptable prodrugs or salts thereof, may contain one or more chiral centers, and thus exist as one or more stereoisomers. Such stereoisomers can be prepared and/or isolated as a single enantiomer, a mixture of diastereomers, or a racemic mixture. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

Formulations can also contain a combination of one or more of the following: cerivastatin, an analog of cerivastatin, a prodrug of cerivastatin, a prodrug of a cerivastatin analog, a salt of cerivastatin, a salt of a cerivastatin analog, a salvate of cerivastatin, a solvate of a cerivastatin analog, a clathrate of cerivastatin, and a clathrate of a cerivastatin analog.

2. Other Active Agents

Formulations for the treatment of pulmonary arterial hypertension can also contain one or more additional active agents, Preferably, the one or more additional active agents are useful for the treatment of a pulmonary disease. Suitable additional active agents include, but are not limited, to bronchodilators, vasodilators, phosphodiesterase inhibitors, endothelin receptor antagonists, cerivastatinal anti-inflammatory drugs, and non-cerivastatinal anti-inflammatory drugs.

In some cases, the formulation contains one or more bronchodilators which provides anti-inflammatory action and assists in the delivery of an inhaled formulation deep into the lungs. Suitable bronchodilators include β-2 agonists (e.g., albuterol, levalbuterol (i.e., homochiral R-albuterol), terbutaline, pirbuterol, fenoterol, salmeterol, formoterol, bambuterol, clenbuterol, or idacaterol), anticholinergics (e.g., ipratropium bromide, oxitropium bromide, tiotropium bromide, or glycopyrrolate), In some cases, the formulation contains one or more phosphodiesterase (PDE) inhibitors. The PDE inhibitors can be nonspecific PDE inhibitors including, for example, aminophylline and paraxanthine, PDE-1 selective inhibitors such as vinpocetine, PDE-2 selective inhibitors such as erythro-9-(2-hydroxy-3-nonyl)adenine) and anagrelide, PDE-3 selective inhibitors such as enoximone, PDE-4 selective inhibitors such as ibudilast, piclamilast, luteolin, and roflumilast, or PDE-5 selective inhibitors such as sildenafil, tadalafil, vardenafil, udenafil, avanafil, dipyridamole, and icariin.

In some cases, the formulation contains one or more prostaglandins suitable for pulmonary administration, such as iloprost or treprostinil In some cases, the formulation contains one or more endothelin receptor antagonists, such as bosentan, sitaxentan, or ambrisentan.

In some cases, the formulation can include one or more activators of soluble guanylate cyclase, such as cinaciguat or riociguat.

In some cases, the formulation can include one or more inhaled corticosteroid such as flunisolide, triamcinolone acetonide, beclomethasone dipropionate, mometasone, budesonide, ciclesonide, or fluticasone propionate.

In some cases, the formulation can include one or more antibiotics which are known to possess anti-inflammatory activity, such as erythromycin, azithromycin, or clarithromycin.

In some cases, the formulation can include one or more anticoagulants. Suitable anticoagulants include vitamin K antagonists (i.e., coumarins such as warfarin or dicoumarol and 1,3-indandione derivatives) and direct thrombin inhibitors.

B. Formulations for Pulmonary Administration

An effective amount of cerivastatin, an analog of cerivastatin, or a pharmaceutically acceptable prodrug, salt, solvate, or clathrate thereof to treat or prevent pulmonary arterial hypertension can be formulation for systemic administration (i.e., enteral or parenteral administration). However, when administered systemically, cerivastatin can cause potentially fatal side-effects, including rhabdomyolysis. To minimize the undesirable side effects associated with the systemic administration of cerivastatin, cerivastatin, an analog of cerivastatin, or a pharmaceutically acceptable prodrug, salt, solvate, or clathrate thereof is preferably formulated to provide for localized administration of an effective amount of cerivastatin to treat or prevent PAH directly to the lungs.

Formulations contain an effective amount of cerivastatin, an analog of cerivastatin, or a pharmaceutically acceptable prodrug, salt, solvate, or clathrate thereof in a pharmaceutical carrier appropriate for pulmonary administration. Pharmaceutical formulations and methods for the pulmonary administration of low molecular weight active agents is known in the art. For example, beta-androgenic antagonists and cerivastatins are frequently administered via inhalation to treat pulmonary conditions, including asthma.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

The alveolar surface area is the largest in the respiratory system and is where drug absorption occurs. The alveoli are covered by a thin epithelium without cilia or a mucus blanket and secrete surfactant phospholipids. Effective delivery of therapeutic agents via pulmonary routes requires that the active agent be formulated so as to reach the alveoli.

In the case of pulmonary administration, formulations can be divided into dry powder formulations and liquid formulations. Both dry powder and liquid formulations can be used to form aerosol formulations. The term aerosol as used herein refers to any preparation of a fine mist of particles, which can be in solution or a suspension, whether or not it is produced using a propellant.

Useful formulations, and methods of manufacture, are described by Caryalho, et al., J Aerosol Med Pulm Drug Deliv. 2011 Apr.; 24(2):61-80. Epub 2011 Mar. 16, for delivery of chemotherapeutic drugs to the lungs.

1. Dry Powder Formulations

Dry powder formulations are finely divided solid formulations containing one or more active agents which are suitable for pulmonary administration. In dry powder formulations, the one or more active agents can be incorporated in crystalline or amorphous form.

Dry powder formulations include, at a minimum, cerivastatin, an analog of cerivastatin, or a pharmaceutically acceptable prodrug, salt, solvate, or clathrate thereof. Such dry powder formulations can be administered via pulmonary inhalation to a patient without the benefit of any carrier, other than air or a suitable propellant. Preferably, however, the dry powder formulations contain cerivastatin, an analog of cerivastatin, or a pharmaceutically acceptable prodrug, salt, solvate, or clathrate thereof in combination with a pharmaceutically acceptable carrier.

The pharmaceutical carrier may include a bulking agent, such as carbohydrates (including monosaccharides, polysaccharides, and cyclodextrins), polypeptides, amino acids, and combinations thereof. Suitable bulking agents include fructose, galactose, glucose, lactitol, lactose, maltitol, maltose, mannitol, melezitose, myoinositol, palatinite, raffinose, stachyose, sucrose, trehalose, xylitol, hydrates thereof, and combinations thereof.

The pharmaceutical carrier may include a lipid or surfactant. Natural surfactants such as dipalmitoylphosphatidylcholine (DPPC) are the most preferred. This is commercially available for treatment of respiratory distress syndrome in premature infants. Synthetic and animal derived pulmonary surfactants include:

Synthetic Pulmonary Surfactants

Exosurf—a mixture of DPPC with hexadecanol and tyloxapol added as spreading agents Pumactant (Artificial Lung Expanding Compound or ALEC)—a mixture of DPPC and PG KL-4—composed of DPPC, palmitoyl-oleoyl phosphatidylglycerol, and palmitic acid, combined with a 21 amino acid synthetic peptide that mimics the structural characteristics of SP-B.

Venticute—DPPC, PG, palmitic acid and recombinant SP-C

Animal Derived Surfactants

Alveofact—extracted from cow lung lavage fluid

Curosurf—extracted from material derived from minced pig lung

Infasurf—extracted from calf lung lavage fluid

Survanta—extracted from minced cow lung with additional DPPC, palmitic acid and tripalmitin Exosurf, Curosurf, Infasurf, and Survanta are the surfactants currently FDA approved for use in the U.S.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

Dry powder formulations are typically prepared by blending cerivastatin, an analog of cerivastatin, or a pharmaceutically acceptable prodrug, salt, solvate, or clathrate thereof with a pharmaceutical carrier. Optionally, additional active agents may be incorporated into the mixture as discussed above. The mixture is then formed into particles suitable for pulmonary administration using techniques known in the art, such as lyophilization, spray drying, agglomeration, spray coating, extrusion processes, hot melt particle formation, phase separation particle formation (spontaneous emulsion particle formation, solvent evaporation particle formation, and solvent removal particle formation), coacervation, low temperature casting, grinding, milling (e.g., air-attrition milling (jet milling), ball milling), high pressure homogenization, and/or supercritical fluid crystallization.

An appropriate method of particle formation can be selected based on the desired particle size, particle size distribution, and particle morphology. In some cases, the method of particle formation is selected so as to produce a population of particles with the desired particle size, particle size distribution for pulmonary administration. Alternatively, the method of particle formation can produce a population of particles from which a population of particles with the desired particle size, particle size distribution for pulmonary administration is isolated, for example by sieving.

It is known in the art that particle morphology affects the depth of penetration of a particle into the lung as well as uptake of the drug particles. As discussed above, drug particles should reach the alveoli to maximize therapeutic efficacy. Accordingly, dry powder formulations is processed into particles having the appropriate mass median aerodynamic diameter (MMAD), tap density, and surface roughness to achieve delivery of the one or more active agents to the deep lung. Preferred particle morphologies for delivery to the deep lung are known in the art, and are described, for example, in U.S. Pat. No. 7,052,678 to Vanbever, et al.

Particles having a mass median aerodynamic diameter (MMAD) of greater than about 5 microns generally do not reach the lung; instead, they tend to impact the back of the throat and are swallowed. Particles having diameters of about 3 to about 5 microns are small enough to reach the upper- to mid-pulmonary region (conducting airways), but may be too large to reach the alveoli. Smaller particles, (i.e., about 0.5 to about 3 microns), are capable of efficiently reaching the alveolar region. Particles having diameters smaller than about 0.5 microns can also be deposited in the alveolar region by sedimentation, although very small particles may be exhaled.

The precise particle size range effective to achieve delivery to the alveolar region will depend on several factors, including the tap density of particles being delivered. Generally speaking, as tap density decreases, the MMAD of particles capable of efficiently reaching the alveolar region of the lungs increases. Therefore, in cases of particles with low tap densities, particles having diameters of about 3 to about 5 microns, about 5 to about 7 microns, or about 7 to about 9.5 microns can be efficiently delivered to the lungs. The preferred aerodyanamie diameter for maximum deposition within the lungs can be calculated. See, for example, U.S. Pat. No. 7,052,678 to Vanbever, et al.

In some embodiments, the dry powder formulation is composed of a plurality of particles having a median mass aerodynamic diameter between about 0.5 to about 10 microns, more preferably between about 0.5 microns to about 7 microns, most preferably between about 0.5 to about 5 microns. In some embodiments, the dry powder formulation is composed of a plurality of particles having a median mass aerodynamic diameter between about 0.5 to about 3 microns. In some embodiments, the dry powder formulation is composed of a plurality of particles having a median mass aerodynamic diameter between about 3 to about 5 microns. In some embodiments, the dry powder formulation is composed of a plurality of particles having a median mass aerodynamic diameter between about 5 to about 7 microns. In some embodiments, the dry powder formulation is composed of a plurality of particles having a median mass aerodynamic diameter between about 7 to about 9.5 microns.

In some cases, there may be an advantage to delivering particles larger than about 3 microns in diameter. Phagocytosis of particles by alveolar macrophages diminishes precipitously as particle diameter increases beyond about 3 microns. Kawaguchi, H., et al., Biomaterials 7: 61-66 (1986); Krenis, L. J. and Strauss, B., Proc. Soc. Exp. Med., 107: 748-750 (1961); and Rudt, S. and Muller, R. H., J. Contr. Rel, 22: 263-272 (1992). By administering particles with an aerodynamic volume greater than 3 microns, phagocytic engulfment by alveolar macrophages and clearance from the lungs can be minimized.

In some embodiments, at least about 80%, more preferably at least about 90%, most preferably at least about 95% of the particles in dry powder formulation have aerodynamic diameter of less than about 10 microns, more preferably less than about 7 microns, most preferably about 5 microns. In some embodiments, at least about 80%, more preferably at least about 90%, most preferably at least about 95%, of the particles in dry powder formulation have aerodynamic diameter of greater than about 0.5 microns. In some embodiments, at least about 80%, more preferably at least about 90%, most preferably at least about 95%, of the particles in dry powder formulation have an aerodynamic diameter of greater than about 0.1 microns.

In some embodiments, at least about 80%, more preferably at least about 90%, most preferably at least about 95%, of the particles in dry powder formulation have aerodynamic diameter of greater than about 0.5 microns and less than about 10 microns, more preferably greater than about 0.5 microns and less than about 7 microns, most preferably greater than about 0.5 microns and less than about 5 microns. In some embodiments, at least about 80%, more preferably at least about 90%, most preferably at least about 95% of the particles in dry powder formulation have aerodynamic diameter of greater than about 0.5 microns and less than about 3 microns. In some embodiments, at least about 80%, more preferably at least about 90%, most preferably at least about 95% of the particles in dry powder formulation have aerodynamic diameter of greater than about 3 microns and less than about 5 microns. In some embodiments, at least about 80%, more preferably at least about 90%, most preferably at least about 95% of the particles in dry powder formulation have aerodynamic diameter of greater than about 5 microns and less than about 7 microns. In some embodiments, at least about 80%, more preferably at least about 90%, most preferably at least about 95% of the particles in dry powder formulation have aerodynamic diameter of greater than about 7 microns and less than about 9.5 microns.

In some embodiments, the particles have a tap density of less than about 0.4 g/cm$^3$, more preferably less than about 0.25 g/cm$^3$, most preferably less than about 0.1 g/cm$^3$. Features which can contribute to low tap density include irregular surface texture and porous structure.

In some cases, the particles are spherical or ovoid in shape. The particles can have a smooth or rough surface texture. The particles may also be coated with a polymer or other suitable material to control release of one or more active agents in the lungs.

Dry powder formulations can be administered as dry powder using suitable methods known in the art. Alternatively, the dry powder formulations can be suspended in the liquid formulation s described below, and administered to the lung using methods known in the art for the delivery of liquid formulations.

2. Liquid Formulations

Liquid formulations contain cerivastatin, an analog of cerivastatin, or a pharmaceutically acceptable prodrug, salt, solvate, or clathrate thereof dissolved or suspended in a liquid pharmaceutical carrier.

Suitable liquid carriers include, but are not limited to distilled water, de-ionized water, pure or ultrapure water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human.

Preferably, liquid formulations are isotonic relative to physiological fluids and of approximately the same pH, ranging e.g., from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

In some cases the liquid formulation may contain one or more solvents that are low toxicity organic (i.e. nonaqueous) class 3 residual solvents, such as ethanol, acetone, ethyl acetate, tetrahydofuran, ethyl ether, and propanol. These solvents can be selected based on their ability to readily aerosolize the formulation. Any such solvent included in the liquid formulation should not detrimentally react with the one or more active agents present in the liquid formulation. The solvent should be sufficiently volatile to enable formation of an aerosol of the solution or suspension. Additional solvents or aerosolizing agents, such as a freon, alcohol, glycol, polyglycol, or fatty acid, can also be included in the liquid formulation as desired to increase the volatility and/or alter the aerosolizing behavior of the solution or suspension.

Liquid formulations may also contain minor amounts of polymers, surfactants, or other excipients well known to those of the art. In this context, "minor amounts" means no excipients are present that might adversely affect uptake of the one or more active agents in the lungs.

3. Aerosol Formulations

The dry powder and liquid formulations described above can be used to form aerosol formulations for pulmonary administration. Aerosols for the delivery of therapeutic agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment.

Preferably, a dry powder or liquid formulation as described above is formulated into aerosol formulations using one or more propellants. Suitable propellants include air, hydrocarbons, such as pentane, isopentane, butane, isobutane, propane and ethane, carbon dioxide, chlorofluorocarbons, fluorocarbons, and combinations thereof. Suitable fluorocarbons include 1-6 hydrogen containing fluorocarbons, such as $CHF_2CHF_2$, $CF_3CH_2F$, $CH_2F_2CH_3$, and $CF_3CHFCF_3$ as well as fluorinated ethers such as $CF_3$—O—$CF_3$, $CF_2H$—O—$CHF_2$, and $CF_3$—$CF_2$—O—$CF_2$—$CH_3$. Suitable fluorocarbons also include perfluorocarbons, such as 1-4 carbon perfluorocarbons including $CF_3CF_3$, $CF_3CF_2CF_3$, and $CF_3CF_2CF_2CF_3$.

Preferably, the propellants include, but not limited to, one or more hydrofluoroalkanes (HFA). Suitable HFA propellants, include but are not limited to, 1,1,1,2,3,3,-heptafluoro-n-propane (HFA 227), 1,1,1,2-tetrafluoroethane (HFA 134) 1,1,1,2,25 3,3,3-heptafluoropropane (Propellant 227), or any mixture of these propellants.

Preferably, the one or more propellants have sufficient vapor pressure to render them effective as propellants. Preferably, the one or more propellants are selected so that the density of the mixture is matched to the density of the particles in the aerosol formulation in order to minimize settling or creaming of the particles in the aerosol formulation.

The propellant is preferably present in an amount sufficient to propel a plurality of the selected doses of the aerosol formulation from an aerosol canister.

4. Enhanced Solubilized Cerivastatins

A variety of methods can be employed to enhance the solubility and bioavailability of cerivastatins. See, for example, "Water-Insoluble Drug Formulation", 2nd Edition, edited by Rong Liu (CRC Press, Boca Raton, Fla., 2008). These solubilized formulations can be used as described below, or can be further incorporated into the parenteral and non-parenteral formulations described in sections 2 and 3.

a. Inclusion Complexes

The solubility of cerivastatins can be improved by inclusion complexation (i.e., host-guest formulations). Inclusion complexes are formed when a nonpolar molecule (i.e., the guest, such as a drug with poor aqueous stability) or portion of a molecule inserts into a nonpolar cavity of another molecule or group of molecules (i.e., the host). If the host molecule or molecules exhibit water good solubility, the solubility of the host-guest complex is greater than the solubility of the guest alone.

Inclusion complexes containing one or more cerivastatins can be formed using any suitable host molecule or molecules. For example, the water solubility of cerivastatins can be increased by inclusion complexation with cyclodextrins. Cerivastatin-cyclodextrin inclusion complexes are known in the art. See, for example, U.S. Pat. No. 7,569,557 to Backensfeld, et al., and U.S. Patent Application Publication No. US 2006/0058262 to Zoppetti, et al. Cyclodextrins are cyclic oligosaccharides containing six (α-cyclodextrin), seven (β-cyclodextrin), eight (γ-cyclodextrin), or more α-(1,4)-linked glucose residues. The hydroxyl groups of the cyclodextrins are oriented to the outside of the ring while the glucosidic oxygen and two rings of the non-exchangeable hydrogen atoms are directed towards the interior of the cavity. As a result, cyclodextrins possess a hydrophobic inner cavity combined with a hydrophilic exterior which conveys water solubility. Upon combination with a hydrophobic drug, such as a cerivastatin, the cerivastatin (i.e., the guest) inserts into the hydrophobic interior of the cyclodextrin (i.e., the host). The host-guest complex retains water solubility as a consequence of the hydrophobic exterior of the cyclodextrin ring.

Cerivastatin-cyclodextrin complexes are preferably formed from a cyclodextrin such as an α-cyclodextrin, β-cyclodextrin, γ-cyclodextrin, and derivatives thereof. The cyclodextrin may be chemically modified such that some or all of the primary or secondary hydroxyl groups of the macrocycle, or both, are functionalized with a pendant group. Suitable pendant groups include, but are not limited to, sulfinyl, sulfonyl, phosphate, acyl, and $C_1$-$C_{12}$ alkyl groups optionally substituted with one or more (e.g., 1, 2, 3, or 4) hydroxy, carboxy, carbonyl, acyl, oxy, oxo; or a combination thereof. Methods of modifying these alcohol residues are known in the art, and many cyclodextrin derivatives are commercially available.

Examples of suitable cyclodextrins for use in cerivastatin formulations include α-cyclodextrin; β-cyclodextrin; γ-cyclodextrin; methyl α-cyclodextrin; methyl β-cyclodextrin; methyl γ-cyclodextrin; ethyl β-cyclodextrin; butyl α-cyclodextrin; butyl β-cyclodextrin; butyl γ-cyclodextrin; pentyl γ-cyclodextrin; hydroxyethyl β-cyclodextrin; hydroxyethyl γ-cyclodextrin; 2-hydroxypropyl α-cyclodextrin; 2-hydroxypropyl β-cyclodextrin; 2-hydroxypropyl γ-cyclodextrin; 2-hydroxybutyl β-cyclodextrin; acetyl α-cyclodextrin; acetyl β-cyclodextrin; acetyl γ-cyclodextrin; propionyl β-cyclodextrin; butyryl β-cyclodextrin; succinyl α-cyclodextrin; succinyl β-cyclodextrin; succinyl γ-cyclodextrin; benzoyl β-cyclodextrin; palmityl β-cyclodextrin; toluenesulfonyl β-cyclodextrin; acetyl methyl β-cyclodextrin; acetyl butyl β-cyclodextrin; glucosyl α-cyclodextrin; glucosyl β-cyclodextrin; glucosyl γ-cyclodextrin; maltosyl α-cyclodextrin; maltosyl β-cyclodextrin; maltosyl γ-cyclodextrin; α-cyclodextrin carboxymethylether; β-cyclodextrin carboxymethylether; γ-cyclodextrin carboxymethylether; carboxymethylethyl β-cyclodextrin; phosphate ester α-cyclodextrin; phosphate ester β-cyclodextrin; phosphate ester γ-cyclodextrin; 3-trimethylammonium-2-hydroxypropyl β-cyclodextrin; sulfobutyl ether β-cyclodextrin; carboxymethyl α-cyclodextrin; carboxymethyl β-cyclodextrin; carboxymethyl γ-cyclodextrin, and combinations thereof. Preferred cyclodextrins include, but are not limited to, alkyl cyclodextrins, hydroxy alkyl cyclodextrins, such as hydroxy propyl β-cyclodextrin, carboxy alkyl cyclodextrins and sulfoalkyl ether cyclodextrins, such as sulfo butyl ether β-cyclodextrin. A particularly preferred formulation contains a therapeutically effective amount of one or more cerivastatins in combination with sulfo butyl ether β-cyclodextrin.

Preferably, the cyclodextrin is present in an amount of from about 0.1% to about 40% w/w of the overall formulation, more preferably from about 0.1% to about 25% w/w of the overall formulation.

See also Okamoto, et al., J. Control. Release 150(2):187-95 (2011); Pourshahab, et al. J. Microencapsulation 2011 Jul. 27. [Epub ahead of print]; Preparation and characterization of spray dried inhalable powders containing chitosan nanoparticles for pulmonary delivery of isoniazid; and Gupta, et al. Pharm. Res. 28(7):1733-49 (2011)

b. Particle Size Reduction

The solubility of one or more cerivastatins can be improved by decreasing drug particle size. By decreasing particle size, the surface area to volume ratio of the drug particles is increased, resulting in increased solvation of the drug particle.

Particle size reduction can be achieved using a variety of micronization techniques including, but not limited to, grinding, milling (e.g., air-attrition milling (jet milling), ball milling), coacervation, high pressure homogenization, spray drying, and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). After micronization, the drug particles can be further processed. For example, the micronized drug particles may be coated to further influence solubility and/or drug release.

Depending on the micronization process and active agent involved, the micronized drug particles can be crystalline or amorphous. Using micronization techniques, drug particles ranging from 10 nm to 100 microns can be formed. The average particle size and distribution of the drug particles can be controlled through the selection of micronization technique as well as by variation of process conditions. Accordingly, formulations of drug particles can be prepared which contain nanoparticles of drug, microparticles of drug, and combinations thereof. Appropriate micronization techniques can be selected to produce populations of drug particles with monodisperse or polydisperse particle size distributions. Methods of producing monodisperse drug particles are known in the art. Alternatively, populations of drug particles can be separated following micronization to obtain drug particle populations with the desired size range and distribution.

In addition to improving solubility, micronization can also be used to control drug release profiles. As different sized drug particles will dissolve at different rates and over different periods of time, micronization can be used to prepare controlled release, sustained release, pulsatile release, and delayed release formulations. For example, populations of micronized drug particles with different average particle sizes and/or different particle size distributions can be mixed. The resulting mixtures will exhibit a drug release profile which is the combination of the drug release profile of component populations of drug particles. In some embodiments, micronized drug particles containing different cerivastatins can be mixed to effect combination therapy.

Micronized drug particles can be incorporated into parenteral or non-parenteral formulations as a suspension or dispersion in a solid or fluid carrier. Micronized drug particles can also be used to form solutions for parenteral or non-parenteral administration. Micronized drug particles can also be provided, for example, in a kit used to prepare solutions or suspensions for injection.

2. Lipid Carriers

A variety of lipid carriers may be used to facilitate the administration of cerivastatins possessing poor aqueous solubility, a variety of lipid carriers may be used.

a. Lipid Emulsions

Cerivastatins can be combined suspended or dissolved using a lipid emulsion. Lipid emulsions are known in the art. See, for example, U.S. Pat. No. 6,361,792 to Long, et. al.; U.S. Pat. No. 7,550,155 to Zhang, et al., and U.S. Patent Application Publication No. US 2006/0067952. Lipid emulsions formulations typically include one or more cerivastatins, an oil component, an emulsifier, and water.

The oil component can be a monoglyceride, a diglyceride, a triglyceride, or combinations thereof. In some cases, the oil component includes an ester formed between one or more fatty acids and an alcohol other than glycerol. The oil component can be, for example, a vegetable oil such as almond oil, borage oil, black currant seed oil, corn oil, safflower oil, soybean oil, sesame oil, cottonseed oil, peanut oil, olive oil, rapeseed oil, coconut oil, palm oil, canola oil, or combinations thereof. Vegetable oils are typically long-chain triglycerides formed from $C_{14}$-$C_{22}$ fatty acids. The oil component can also include medium chain triglycerides formed from C8-C12 fatty acids, such as Miglyol 812, Crodamol® GTCC-PN, or Neobees M-5 oil.

The emulsifier serves to stabilize the lipid emulsion by preventing separation of the emulsion into individual oil and aqueous phases. Suitable emulsifiers include, but are not limited to, propylene glycol mono- and di-fatty acid esters, polyoxyethylene sorbitan fatty acid esters, polyoxyethylene fatty acid esters, polyoxyethylene-polyoxypropylene co-polymers and block co-polymers, salts of fatty alcohol sulphates, sorbitan fatty acid esters, esters of polyethylene-glycol glycerol ethers, oil and wax based emulsifiers, glycerol monostearate, glycerine sorbitan fatty acid esters and phospholipids. In some cases the emulsifier is a phospholipid.

In some cases, the emulsifier is a vitamin E derivative. Suitable vitamin E derivatives include, but are not limited to, α-tocopheryl oxalate, α-tocopheryl malonate, α-tocopheryl succinate, α-tocopheryl glutarate, α-tocopheryl adipate, α-tocopheryl pimelate, α-tocopheryl suberate, α-tocopheryl azelate, and D-α-tocopheryl polyethylene glycol 1000 succinate (vitamin E TPGS).

Exemplary phospholipids include, but are not limited to, phosphatidyl chlorine, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. Preferably, the phospholipid is of natural origin. Naturally occurring phospholipids include soy lecithin, egg lecithin, hydrogenated soy lecithin, hydrogenated egg lecithin, sphingosine, gangliosides, and phytosphingosine, and combinations thereof.

Suitable lipid emulsions generally contain between about 1% and 40% w/v oil component and between about 0.1% and 7.5% w/v emulsifier. Suitable commercially available lipid emulsions include lipid emulsions containing soybean oil, such as Intralipid® 10%, Intralipid® 20%, and Intralipid® 30%, and as well as lipid emulsions containing a mixture of soybean and safflower oils, such as Liposyn® II 10% and Liposyn® II 20%.

Lipid emulsions can optionally contain one or more additional components. For example, lipid formulations can contain one or more non-aqueous miscible co-solvents, such as an alcohol or glycol. In some preferred formulations, glycerol and/or propylene glycol is present as a co-solvent.

Many lipid emulsions are capable of supporting bacterial growth. Accordingly, in some cases, one or more components may be added to the lipid emulsion formulation to prevent or retard bacterial growth, for example disodium edatate, citric acid, metabisulfate, benzyl alcohol, one or more parabens, chlorobutanol, phenol, sorbic acid, or thimerosal.

Additionally, lipid emulsions can contain one or more agents used to modify or stabilize the pH of the solution, including phosphate buffers, acetate buffers, and citrate buffers.

In one embodiment, the formulation is an oil-in-water emulsion containing a therapeutically effective amount of one or more cerivastatins dissolved in a solution containing between about 1% w/v and about 25% w/v soybean oil, between about 0.5% and about 7.5% w/v egg yolk phospholipid, and between about 0.5% w/v and about 5% w/v of a miscible co-solvent. In another embodiment, the formulation is an oil-in-water emulsion containing a therapeutically effective amount of one or more cerivastatins dissolved in a solution containing between about 1% w/v and about 15% w/v soybean oil, between about 1% w/v and about 15% w/v safflower oil, between about 0.5% and about 7.5% w/v egg phosphatides, and between about 0.5% w/v and about 5% w/v of a miscible co-solvent.

Lipid nanoemulsions can also be used. Lipid nanoemulsions are known in the art. See, for example, U.S. Patent Application Publication No. US 2007/0207173 to Chen, et al, and U.S. Patent Application Publication No. US 2001/0045050 to Elbayoumi, et al. Lipid nanoemulsions can be prepared by microemulsification of any of the lipid emulsions described above using for example, a high pressure homogenizer, or via a phase inversion temperature method (PIT). In preferred lipid nanoemulsions containing cerivastatins, vitamin E succinate and/or Vitamin E TPGS are included as emulsifiers. The lipid nanoemulsion can further be lyophilized if desired. See, for example, U.S. Patent Publication No. US 2011/0015266. Nanoemulsions typically include an oil phase which has at least one fatty acid oil. Preferable polyunsaturated fatty acids include eicosapentaenoic acid, salts of eicosapentaenoic acid, docosahexaenoic acid, salts of docosahexaenoic acid, triglycerides of eicosapentaenoic acid, tryglycerides of docosahexaenoic acid, ethyl esters of eicosapentaenoic acid, or ethyl esters of docosahexaenoic acid. The nanoemulsion also includes at least one or more surfactants. Surfactants include any molecule having both a polar head group, which energetically prefers solvation by water, and a hydrophobic tail that is not well solvated by water. The ratio of the oil phase to the emulsifier component is important for the toxicity of the nanoemulsion prepared from the pre-concentrate. The surfactant can be provided in either the aqueous or the oil phase. Surfactants suitable for use include a variety of anionic and nonionic surfactants, as well as other emulsifying compounds that are capable of promoting the formation of oil-in-water emulsions; so long as they are on the GRAS (Generally Recognized as Safe) list and are approved for human consumption such as lecithin, solutol HS-15 (polyoxyethylene esters of 12-hydroxystearic acid), polysorbate 80 or Cremophore EL (polyethoxylated castor oil). In general, emulsifying compounds are relatively hydrophilic, and blends of emulsifying compounds can be used to achieve the necessary qualities. In some parenteral formulations, nonionic surfactants have advantages over ionic emulsifiers in that they are substantially more compatible with a broad pH range and often form more stable emulsions than do ionic (e.g., soap-type) emulsifiers. Non-ionic surfactants which are particularly preferred include polyethoxylated hydrogenated castor oil containing 35 mol of ethylene oxide (hereafter referred to as "with 35 EO"), polyethoxylated hydrogenated castor oil containing 7 mol of ethylene oxide (or with 7 EO), polyethoxylated olive oil with 7 EO, sorbitan monooleates with 4 EO, 5 EO or 20 EO, ($C_{12}$-$C_{14}$-alkyl) glycosides or ($C_8$-$C_{14}$alkyl)glycosides, glycerol monostearate with 30 EO, decaglyceryl monooleate, polyalkoxylated oleyl alcohol with 2 or 10 EO, polyethoxylated lauryl alcohol with 7 EO, methylglucoside dioleate, and mixtures thereof. Polyethoxylated castor oil-based emusifiers, such as cremophore EL or the less sensitizing solutol HS-15, are most preferred. Long chain ethoylated surfactants such as Cremophore EL 35, polyethoylated castor oil, a BASF product, TPGS1000, polyethyleneglycol 1000 ester of alpha-tocopheryl succinate, TWEEN® 80, or polyoxyethylene 20 sorbitan monooleate may also be employed as the surfactant. Vitamin E TPGS or PEGylated vitamin E in which polyethylene glycol subunits are attached by a succinic acid diester at the ring hydroxyl of the vitamin E molecule may also be used. TPGS stands for Dα-tocopherol polyethyleneglycol 1000 succinate (MW=530). TPGS is a non-ionic surfactant having an HLB value between 16 and 18.

HLB as used herein refers to the Hydrophile-Lipophile Balance Index Number and is an index for correlating the chemical structure of surfactant molecules with their surface activity. The HLB Index Number may be calculated by a variety of empirical formulas as described by Meyers, (Meyers, Surfactant Science and Technology, VCH Publishers Inc., New York, pp. 231-245 [1992]). The HLB Index Number of a surfactant is the HLB Index Number assigned to that surfactant in McCutcheon's Volume 1: Emulsifiers and Detergents North American Edition, 1996. The HLB Index Number ranges from 0 to about 20 or more for commercial surfactants. Hydrophilic surfactants with high solubility in water and solubilizing properties are at the high end of the scale, while surfactants with low solubility in water that are good solubilizers of water in oils are at the low end of the scale.

b. Liposomes

One or more cerivastatins can be incorporated into liposomes. Liposomes are generally derived from phospholipids or other lipid substances. See, for example, "Remington—The science and practice of pharmacy", 20th Edition, Jennaro et. al., (Philadelphia, Lippencott, Williams, and Wilkens, 2000). Liposomes are formed by mono- or multi-lamellar hydrated liquid crystals that are dispersed in an aqueous medium. The liposomes can be formed using any nontoxic, physiologically acceptable and metabolizable lipid capable of forming liposomes. The liposomal formulations also can contain stabilizers and preservatives.

Methods of forming liposomes are known in the art. See, e.g., Prescott, Ed., Methods in Cell Biology, Volume XIV, Academic Press, New York p. 33 et seq., 1976. Examples of suitable lipids include phospholipids and the phosphatidylcholines (lecithins), both natural and synthetic. The liposomes can be cationic liposomes (e.g., DOTMA, DOPE, DC cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Liposomes are described by Brigham, et al., Am J. Resp Cell. Mol. Biol. 1:95-100,1989; Feigner, et al., Proc. Natl Acad. Sci USA 84:7413-7,1987; and U.S. Pat. No. 4,897,355. Commercially available liposome preparations include LIPOFECTIN®, LIPOFECTAMIE®, (GIBCO-BRL, Inc., Gaithersburg, Md.), SUPERFECT® (Qiagen, Inc. Hilden, Germany) and TRANSFECTAM® (Promega Biotec, Inc., Madison, Wis.), as well as other liposomes developed according to procedures standard in the art.

Noisomes are multilamellar or unilamellar vesicles formed with non-ionic surfactants. An aqueous solution of solute is enclosed by a bilayer resulting from the organization of surfactant macromolecules.

See also Schleh, et al. Eur J. Pharm Biopharm. 77(3):350-2 (2011); Craparo, et al., Int J. Pharm. 15;406(1-2):135-44 (2011) and Zhang, et al., Pharmazie 66(7):496-505 (2011) for lipid or phospholipid enhanced delivery to the lung. See also Gill, et al. Eur. J. Pharm Biopharm 2011 May 7. [Epub ahead of print] Paclitaxel loaded PEG(5000)-DSPE micelles as pulmonary delivery platform.

3. Solid Dispersions

Solid dispersions of cerivastatins can be prepared to enhance water solubility. Solid dispersions are solid-phase mixtures contain one or more cerivastatins in an inert pharmaceutical carrier. To enhance water solubility, the carrier is typically hydrophilic.

Solid dispersions by co-processing one or more cerivastatins in the presence of a carrier using a variety of methods, including the melting (fusion) method, the solvent method, the fusion-solvent method, freeze-drying, and spray drying. Preferred carriers for solid dispersions include polyvinylpyrrolidone (PVP), polyethylene glycols (PEGs), and Plasdone-S630.

A preferred solid dispersion for cerivastatins includes, alone or in part, Human Serum Albumin (HSA) as a carrier. Human serum albumin is a 66-kDa protein found in high concentrations in plasma, where it is used by the body to transport water-insoluble compounds. Owing to numerous disulfide linkages, HSA is relatively stable and can be formulated using conventional methods. Furthermore, HSA does not generally elicit immune responses in vivo.

Solid dispersions can also contain one or more fatty acids, fatty acid conjugates, surfactants, particlularly surfactants with a high HLB value, triglycerides, or other oils. Preferred surfactants include Tween-80, docusate sodium, Myrj-52, Pluronic-F68, and sodium lauryl sulfate.

Solid dispersions may be further processed using additional techniques to enhance solubility, including, for example, micronization or lyophilization.

Solid dispersions may administered as described above, or incorporated into any of the parenteral or non-parenteral formulations described below.

Nanoerythrosomes are delivery devices that can be used to deliver the compositions disclosed herein. Nanoerythrosomes are nano-vesicles made of red blood cells via dialysis through filters of defined pore size. These vesicles can be loaded with a diverse array of biologically active molecules, including proteins and the compositions disclosed herein. They generally serve as ideal carriers for antineoplastic agents like bleomycin, actinomycin D, but can be used for cerivastatins, other lipids, etc.

Artificial red blood cells are generated by interfacial polymerization and complex emulsion methods. Generally, the "cell" wall is made of polyphtaloyl L-lysine polymer/polystyrene and the core is made of a hemoglobin solution from sheep hemolysate. Hemoglobin loaded microspheres typically have particle sizes of from about 1 to about 10 mm. Their size, flexibility, and oxygen carrying capacity is similar to red blood cells.

Solid-lipid nanoparticles are nanoparticles which are dispersed in an aqueous surfactant solution. They are comprised of a solid hydrophobic core having a monolayer of a phospholipid coating and are usually prepared by high-pressure homogenization techniques. Immunomodulating complexes (ISCOMS) are examples of solid lipid nanoparticles. They are cage-like 40 nm supramolecular assemblies comprising of phospholipid, cholesterol, and hydrophobic antigens and are used mostly as immunoadjuvants. ISCOMs are used to prolong blood plasma levels of subcutaneously injected cyclosporine.

Pulmospheres are hollow porous particles with a low density (less than about 0.1 m mL/l). Pulmospheres typically have excellent re-dispersibility and are usually prepared by supercritical fluid condensation technology. Co-spray-drying with certain matrices, such as carbohydrates, human serum albumin, etc., can improve the stability of proteins and peptides (e.g., insulin) and other biomolecules for pulmonary delivery. This type of delivery could be also accomplished with micro-emulsions and lipid emulsions, which are ultra fine, thin, transparent oil-in-water (o/w) emulsions formed spontaneously with no significant input of mechanical energy. In this technique, an emulsion can be prepared at a temperature, which must be higher than the phase inversion temperature of the system. At elevated temperature the emulsion is of water-in-oil (w/o) type and as it cools at the phase inversion temperature, this emulsion is inverted to become o/w. Due to their very small inner phase, they are extremely stable and used for sustained release of cerivastatins and vaccines. Lipid emulsions comprise a neutral lipid core (i.e., triglycerides) stabilized by a monolayer of amphiphilic lipid (i.e., phospholipid) using surfactants like egg lecithin triglycerides and miglyol. They are suitable for passive and active targeting.

4. Controlled Release Formulations

The formulations can be formulated for controlled release including immediate release, delayed release, extended release, pulsatile release, and combinations thereof.

a. Nano- and Microparticles

The cerivastatins and optionally one or more additional active agents, can be incorporated into microparticles (including microspheres and microcapsules), nanoparticles (including nanospheres and nanocapsules), or combinations thereof that provide controlled release. In contrast to liposomal delivery systems, microspheres and micro-capsules typically do not have an aqueous core but a solid polymer matrix or membrane. The encapsulated compound is gradually released from the depot by erosion and/or diffusion from the particles. In embodiments wherein the formulations contains two or more actives, the actives can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.). For example, the compounds and/or one or more additional active agents can be incorporated into polymeric microparticles which provide controlled release of the drug(s). Release of the drug(s) is controlled by diffusion of the drug(s) out of the microparticles and/or degradation of the polymeric particles by hydrolysis and/or enzymatic degradation.

Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to, hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. Rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. These delivery devices are obtained by methods such as controlled precipitation of polymers, chemical cross-linking of soluble polymers, or interfacial polymerization of two monomers or high-pressure homogenization techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. Detailed descriptions of these processes can be found in "Remington—The science and practice of pharmacy", 20th Edition, Jennaro et. al., (Phila, Lippencott, Williams, and Wilkens, 2000).

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., *Biomaterials* 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylase and guar gum are subject to cross-linking in the presence of multivalent cations. Complexes between oppositely charged polysaccharides can also be formed; pectin and chitosan, for example, can be complexed via electrostatic interactions.

Cerivastatin and its analogs can be targeted to inflammatory macrophage in the lung of PAH patients by incorporation into polyketals, a copolymer of 1,4-cyclohexanedimethanol and 1,5-pentanediol. Cerivasatin-polyketal nanoparticles are then delivered to the lung by inhalation. Cerivastatin is release when the polyketal is degraded. Cerivastatin is also delivered by incorporating in the nanoparticles of polymers of poly-(1,4 phenyleneacetone dimethylene thioketal that degrades selectively in response to the oxidative stress in the tissue of PAH patient.

b. Depot Formulations

Cerivastatins, including progesterone and progesterone analogues such ?? as decanoate salts or esters of progesterone, can be formulated for depot injection. In a depot injection, the active agent is formulated with one or more pharmaceutically acceptable carriers that provide for the gradual release of active agent over a period of hours or days after injection. The depot formulation can be administered by any suitable means; however, the depot formulation is typically administered via subcutaneous or intramuscular injection.

A variety of carriers may be incorporated into the depot formulation to provide for the controlled release of the active agent. In some cases, depot formulations contain one or more biodegradable polymeric or oligomeric carriers. Suitable polymeric carriers include, but are not limited to poly(lactic acid) (PLA), poly(lactic-co-glycolic acid) (PLGA), poly(lactic acid)-polyethyleneglycol (PLA-PEG) block copolymers, polyanhydrides, poly(ester anhydrides), polyglycolide (PGA), poly-3-hydroxybutyrate (PHB) and copolymers thereof, poly-4-hydroxybutyrate (P4HB), polycaprolactone, cellulose, hydroxypropyl methylcellulose, ethylcellulose, as well as blends, derivatives, copolymers, and combinations thereof.

In depot formulations containing a polymeric or oligomeric carrier, the carrier and active agent can be formulated as a solution, an emulsion, or suspension. One or more cerivastatins, and optionally one or more additional active agents, can also be incorporated into polymeric or oligomeric microparticles, nanoparticles, or combinations thereof.

In some cases, the formulation is fluid and designed to solidify or gel (i.e., forming a hydrogel or organogel) upon injection. This can result from a change in solubility of the composition upon injection, or for example, by injecting a pre-polymer mixed with an initiator and/or crosslinking agent. The polymer matrix, polymer solution, or polymeric particles entrap the active agent at the injection site. As the polymeric carrier is gradually degraded, the active agent is released, either by diffusion of the agent out of the matrix and/or dissipation of the matrix as it is absorbed. The release rate of the active agent from the injection site can be controlled by varying, for example, the chemical composition, molecular weight, crosslink density, and concentration of the polymeric carrier. Examples of such systems include those described in U.S. Pat. Nos. 4,938,763, 5,480,656 and 6,113,943.

Depot formulations can also be prepared by using other rate-controlling excipients, including hydrophobic materials, including acceptable oils (e.g., peanut oil, corn oil, sesame oil, cottonseed oil, etc.) and phospholipids, ion-exchange resins, and sparingly soluble carriers.

The depot formulation can further contain a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the neuroactive compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

d. Gels

Formulations may be in the form of a hydrogel. Numerous gel formulations are known. See, for example, U.S. Pat. No. 5,411,737 by Hsu, et al. Hydrogels, especially those further including nanoparticles microparticles for sustained, immediate and/or delayed release, can also be used. See, for example, U.S. Pat. No. 6,589,549 to Shih, et al.

U.S. patent application No. 20100295113 by Hoffman, et al., describes a composite hydrogel including a blend of an aqueous solution of an anionic polysaccharide or a derivative thereof, such as or a derivative thereof and an aqueous solution of methylcellulose or another water soluble cellulose derivative thereof, having dispersed polymeric particles, such as polymeric micro particles and nanoparticles, and wherein the stability of the hydrogel is enhanced relative to the stability of the hydrogel alone. The polymeric particles may contain at least one therapeutic agent, in which case each therapeutic agent exhibits a linear sustained release rate that can be tuned or altered by selecting the appropriate polymer formulation of the micro particles and/or nanoparticles. The composite may be injectable, and in the absence of a therapeutic agent may be used as a bulking agent for reconstructive and cosmetic surgery or may act as a platform for subsequent delivery of therapeutic agents.

See also, Salem, *Int J Nanomedicine*. (2010) 10; 5:943-54, describing a sustained release form of natural progesterone to be given as IM injection. A progesterone nanosuspension (PNS) was first developed and then dispersed in a thermosensitive gel matrix. The selected nanoparticles showed an average particle size of 267 nm and a zeta potential approaching-41 mV. The in vitro release profile of PNS from Pluronic F127 plus methyl cellulose gel followed zero order kinetics and correlated linearly with the weight percentage of gel dissolved, demonstrating that the overall rate of release of PNS is controlled by dissolution of the pluronic F127/methyl cellulose (MC) gel.

Gels can also be administered in combination with oral or subcutaneously administered drug. See, for example, Tomic, et al., *Gynecol Endocrinol*. 2011 Apr. 19.

See also the following reviews: Forbes, et al., Adv Drug Deliv Rev. 63(1-2):69-87 (2011); Dolovich, et al. Lancet 19; 377(9770):1032-45 (2011); and Gentile, et al., Curr Opin Pharmacol 10(3):260-5 (2010); Kurmi, et al., Expert Opin Drug Deliv. 7(7):781-94 (2010); Dandekar, et al. J. Aerosol Med. Pulm Deliv 23(6):343-53 (2010); Carvalho, et al., J. Aerosol Med Pulm Drug Deliv. 24(2):61-80 (2011).

5. Targeting

As described by Urakami, et al. Am. J. Pathol. 178(6): 2489-2495 (2011), selective targeting is extremely effective in treating PAH. Highly selective targeting of rat PAH lesions by a cyclic peptide, CARSKNKDC (SEQ ID NO:1) (CAR)), by intravenous administration resulted in intense accumulation of the peptide in monocrotaline-induced and SU5416/hypoxia-induced hypertensive lungs but not in healthy lungs or other organs of PAH rats. CAR homed to all layers of remodeled pulmonary arteries, ie, endothelium, neointima, medial smooth muscle, and adventitia, in the hypertensive lungs. CAR also homed to capillary vessels and accumulated in the interstitial space of the PAH lungs, manifesting its extravasation activity. These results demonstrated the ability of CAR to selectively target PAH lung vasculature and effectively penetrate and spread throughout the diseased lung tissue.

See al. Cao, et al., Drug Deliv. Aug. 4 (2011); Zhonq Yao Cai 32(3):423-6 (2009) targeting to the lung with GM-CSF, and Jain, et al., PDA J. Pharm Sci Technol 64(3):278-87 (2010) (lactose-conjugated PLGA nanoparticles for enhanced delivery to the lung).

III. Methods of Administration

The formulations described above can be administered to a patient in need thereof to treat or prevent pulmonary arterial hypertension.

A. Devices for Pulmonary Administration

To minimize the undesirable side effects associated with the systemic administration of cerivastatin, an effective amount of cerivastatin, an analog of cerivastatin, or a pharmaceutically acceptable prodrug, salt, solvate, or clathrate thereof is preferably administered locally (i.e., directly to the lungs).

In some cases, the one or more active agents are delivered into the lungs by inhalation of an aerosolized pharmaceutical formulation. Inhalation can occur through the nose and/or the mouth of the patient. Administration can occur by self-administration of the formulation while inhaling, or by administration of the formulation via a respirator to a patient on a respirator.

In some cases, a device is used to administer the formulations to the lungs. Suitable devices include, but are not limited to, dry powder inhalers, pressurized metered dose inhalers, nebulizers, and electrohydrodynamic aerosol devices.

1. Dry Powder Inhalers

The dry powder formulations described above can be administered to the lungs of a patient using a dry powder inhaler (DPI). DPI devices typically use a mechanism such as a burst of gas to create a cloud of dry powder inside a container, which can then be inhaled by the patient.

In a dry powder inhaler, the dose to be administered is stored in the form of a non-pressurized dry powder and, on actuation of the inhaler, the particles of the powder are inhaled by the subject. In some cases, a compressed gas (i.e., propellant) may be used to dispense the powder, similar to pressurized metered dose inhalers (pMDIs). In some cases, the DPI may be breath actuated, meaning that an aerosol is created in precise response to inspiration. Typically, dry powder inhalers administer a dose of less than a few tens of milligrams per inhalation to avoid provocation of cough.

DPIs function via a variety of mechanical means to administer formulations to the lungs. In some DPIs, a doctor blade or shutter slides across the dry powder formulation contained in a reservoir, culling the formulation into a flowpath whereby the patient can inhale the powder in a single breath. In other DPIs, the dry powder formulation is packaged in a preformed dosage form, such as a blister, tabule, tablet, or gelcap, which is pierced, crushed, or otherwise unsealed to release the dry powder formulation into a flowpath for subsequent inhalation. Still others DPIs release the dry powder formulation into a chamber or capsule and use mechanical or electrical agitators to keep the dry powder formulation suspended in the air until the patient inhales.

Dry powder formulations may be packaged in various forms, such as a loose powder, cake, or pressed shape for insertion in to the reservoir of a DPI.

Examples suitable DPIs for the administration of the formulations described above include the Turbohaler® inhaler (Astrazeneca, Wilmington, Del.), the Clickhaler® inhaler (Innovata, Ruddington, Nottingham, UK), the Diskus® inhaler (Glaxo, Greenford, Middlesex, UK), the EasyHaler® (Orion, Expoo, FI), the Exubera® inhaler (Pfizer, New York, N.Y.), the Qdose® inhaler (Microdose, Monmouth Junction, N.J.), and the Spiros® inhaler (Dura, San Diego, Calif.).

2. Pressurized Metered Dose Inhalers

The liquid formulations described above can be administered to the lungs of a patient using a pressurized metered dose inhaler (pMDI).

Pressurized Metered Dose Inhalers (pMDIs) generally include at least two components: a canister in which the liquid formulation is held under pressure in combination with one or more propellants, and a receptacle used to hold and actuate the canister. The canister may contain a single or multiple doses of the formulation. The canister may include a valve, typically a metering valve, from which the contents of the canister may be discharged. Aerosolized drug is dispensed from the pMDI by applying a force on the canister to push it into the receptacle, thereby opening the valve and causing the drug particles to be conveyed from the valve through the receptacle outlet. Upon discharge from the canister, the liquid formulation is atomized, forming an aerosol.

pMDIs typically employ one or more propellants to pressurize the contents of the canister and to propel the liquid formulation out of the receptacle outlet, forming an aerosol. Any suitable propellants, including those discussed above, may be utilized. The propellant may take a variety of forms. For example, the propellant may be a compressed gas or a liquefied gas. Chlorofluorocarbons (CFC) were once commonly used as liquid propellants, but have now been banned. They have been replaced by the now widely accepted hydrofluororalkane (HFA) propellants.

pMDIs are available from a number of suppliers, including 3M Corporation, Aventis, Boehringer Ingleheim, Forest Laboratories, Glaxo-Wellcome, Schering Plough and Vectura. In some cases, the patient administers an aerosolized formulation by manually discharging the aerosolized formulation from the pMDI in coordination with inspiration. In this way, the aerosolized formulation is entrained within the inspiratory air flow and conveyed to the lungs.

In other cases, a breath-actuated trigger, such as that included in the Tempo® inhaler (MAP Pharmaceuticals, Mountain View, Calif.) may be employed that simultaneously discharges a dose of the formulation upon sensing inhalation. These devices, which discharge the aerosol formulation when the user begins to inhale, are known as breath-actuated pressurized metered dose inhalers (baMDIs).

3. Nebulizers

The liquid formulations described above can also be administered using a nebulizer. Nebulizers are liquid aerosol generators that convert the liquid formulation described able, usually aqueous-based compositions, into mists or clouds of small droplets, preferably having diameters less than 5 microns mass median aerodynamic diameter, which can be inhaled into the lower respiratory tract. This process is called atomization. The droplets carry the one or more active agents into the nose, upper airways or deep lungs when the aerosol cloud is inhaled. Any type of nebulizer may be used to administer the formulation to a patient, including, but not limited to pneumatic (jet) nebulizers and electromechanical nebulizers.

Pneumatic (jet) nebulizers use a pressurized gas supply as a driving force for atomization of the liquid formulation. Compressed gas is delivered through a nozzle or jet to create a low pressure field which entrains a surrounding liquid formulation and shears it into a thin film or filaments. The film or filaments are unstable and break up into small droplets that are carried by the compressed gas flow into the inspiratory breath. Baffles inserted into the droplet plume screen out the larger droplets and return them to the bulk liquid reservoir. Examples of pneumatic nebulizers include, but are not limited to, PART LC Plus®, PART LC Sprint®, Devilbiss PulmoAide®, and Boehringer Ingelheim Respima®.

Electromechanical nebulizers use electrically generated mechanical force to atomize liquid formulations. The electromechanical driving force can be applied, for example, by vibrating the liquid formulation at ultrasonic frequencies, or by forcing the bulk liquid through small holes in a thin film. The forces generate thin liquid films or filament streams which break up into small droplets to form a slow moving aerosol stream which can be entrained in an inspiratory flow.

In some cases, the electromechanical nebulizer is an ultrasonic nebulizer, in which the liquid formulation is coupled to a vibrator oscillating at frequencies in the ultrasonic range. The coupling is achieved by placing the liquid in direct contact with the vibrator such as a plate or ring in a holding cup, or by placing large droplets on a solid vibrating projector (a horn). The vibrations generate circular standing films which break up into droplets at their edges to atomize the liquid formulation. Examples of ultrasonic nebulizers include DuroMist®, Drive Medical Beetle Neb®, Octive Tech Densylogic®, and John Bunn Nano-Sonic®.

In some cases, the electromechanical nebulizer is a mesh nebulizer, in which the liquid formulation is driven through a mesh or membrane with small holes ranging from 2 to 8 microns in diameter, to generate thin filaments which break up into small droplets. In certain designs, the liquid formulation is forced through the mesh by applying pressure with a solenoid piston driver (for example, the AERx® nebulizer), or by sandwiching the liquid between a piezoelectrically vibrated plate and the mesh, which results in a oscillatory pumping action (for example EFlow®, AerovectRx®, or TouchSpray® nebulizer). In other cases, the mesh vibrates back and forth through a standing column of the liquid to pump it through the holes. Examples of such nebilzers include the AeroNeb Go®, AeroNeb Pro®. PART EFlow®, Omron 22UE®; and Aradigm AERx®.

4. Electrohydrodynamic Aerosol Devices

The liquid formulations described above can also be administered using an electrohydrodynamic (EHD) aerosol device. EHD aerosol devices use electrical energy to aerosolize liquid drug solutions or suspensions. Examples of EHD aerosol devices are known in the art. See, for example, U.S. Pat. No. 4,765,539 to Noakes et al. and U.S. Pat. No. 4,962,885 to Coffee, R. A.

The electrochemical properties of the formulation may be important parameters to optimize when delivering the liquid formulation to the lung with an EHD aerosol device and such optimization is routinely performed by one of skill in the art.

B. Disorders to be Treated

Formulations containing a therapeutically effective amount of cerivastatin, an analog of cerivastatin, or a pharmaceutically acceptable prodrug, salt, solvate, or clathrate thereof are administered to a patient in need thereof to treat or prevent pulmonary arterial hypertension.

A patient in need of treatment can include a patient afflicted with pulmonary arterial hypertension, such as a patient with a resting mean pulmonary arterial pressure (mPAP) of greater than 20 mmHg. A patient in need of treatment can also include a patient who is prone to develop PAH, in which the PAH is to be prevented. Examples of such patients include patients with a family history of PAH, patients one or more risk factors or conditions associated with PAH, and/or patients with one or more pulmonary diseases or disorders.

In some cases, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension that is not linked do any apparent risk factor or condition. This type of PAH is typically classified in clinical settings as idiopathic pulmonary arterial hypertension (IPAH).

In some cases, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension that is inherited (i.e., genetically based). This type of PAH is typically classified in clinical settings as familial pulmonary arterial hypertension (FPAH). In certain embodiments, the patient possesses one or more mutations in the gene encoding the bone morphogenetic protein receptor type II (BMPR2).

In some cases, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension that is associated with one or more risk factors or associated conditions. This type of PAH is typically classified in clinical settings as associated pulmonary arterial hypertension (APAH). In certain embodiments, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension associated with collagen vascular diseases (e.g., scleroderma, lupus erythematosus), congenital systemic-to-pulmonary shunts (including simple, complex, and combined shunts which may be large or small, and may be corrected, partially corrected, or noncorrected), portal hypertension, HIV infection, drug use (e.g., cocaine, anorexigens), toxin exposure, thyroid disorders, glycogen storage diseases, Gaucher's disease, hereditary hemorrhagic telangiectasia, hemoglobinopathies (e.g., sickle cell disease), myeloproliferative disorders, or a splenectomy.

In some cases, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent persistent pulmonary hypertension of the newborn.

In some cases, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension that is associated with significant venous or capillary involvement. In one embodiment, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension associated with pulmonary veno-occlusive disease (PVOD). In one embodiment, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension associated with pulmonary capillary hemangiomatosis (PCH).

In some cases, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension in a patient which is associated with one or more pulmonary diseases or disorders such as chronic obstructive pulmonary disease (COPD), asthma, interstitial lung disease, sleep-disordered breathing, alveolar hypoventilation disorders, and developmental abnormalities. In some cases, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension in a patient which is associated with hypoxemia resulting from chronic exposure to high altitude.

In some cases, a pharmaceutical formulation containing a therapeutically effective amount of cerivastatin, an analog of cerivastatin, or a pharmaceutically acceptable prodrug, salt, solvate, or clathrate thereof is administered to a patient to treat or prevent pulmonary arterial hypertension that is associated with thromboembolic obstruction of proximal pulmonary arteries, thromboembolic obstruction of distal pulmonary arteries, or non-thrombotic pulmonary embolism (e.g., a tumor).

In some cases, a pharmaceutical formulation containing a therapeutically effective amount of cerivastatin, an analog of cerivastatin, or a pharmaceutically acceptable prodrug, salt, solvate, or clathrate thereof is administered prophylactically to patients at risk of developing PAH. In certain cases, a pharmaceutical formulation containing a therapeutically effective amount of cerivastatin, an analog of cerivastatin, or a pharmaceutically acceptable prodrug, salt, solvate, or clathrate thereof is administered prophylactically to patients with a family history of PAH. In some cases, a pharmaceutical formulation containing a therapeutically effective amount of cerivastatin, an analog of cerivastatin, or a pharmaceutically acceptable prodrug, salt, solvate, or clathrate thereof is administered prophylactically to patients possess one or more risk factors for PAH, or have been diagnosed with a disease or disorder which can lead to the development of PAH.

C. Dosage

Formulations containing a therapeutically effective amount of cerivastatin, an analog of cerivastatin, or a pharmaceutically acceptable prodrug, salt, solvate, or clathrate thereof are administered to a patient in need thereof to treat or prevent pulmonary arterial hypertension. A therapeutically effective treatment is one that results in alleviation of one or more symptoms of pulmonary arterial hypertension.

Beneficial or desired clinical results include, but are not limited to, lessening or prevention of pulmonary arterial hypertension, alleviation of one or more symptoms of pulmonary arterial hypertension, decreased resting mean pulmonary arterial pressure (mPAP), decreased right ventricular (RV) wall thickness, increased pulmonary artery acceleration time (PAAT), diminishment of extent of pulmonary artery hypertension, stabilized (i.e., not worsening) state of pulmonary artery hypertension, delayed disease progression, amelioration or palliation of the disease state, and remission (whether partial or total). Treatment can also include the improvement in the quality of life of the patient. Treatment also include the improvement in 6 min walk time of the patient. Treatment can also include prolonging survival as compared to expected survival if not receiving treatment.

The precise dosage administered to a patient will depend on many factors, including the physical characteristics of the patient (e.g., weight), the degree of severity of the pulmonary arterial hypertension, and the presence or absence of other pulmonary or cardiovascular diseases or disorders.

Preferably, the formulation is administered non-systemically (i.e., locally within the lung and lung vasculature) using a device as described above. By administering the formulation locally, therapeutic efficacy can be achieved with a lower dosage of cerivastatin, an analog of cerivastatin, or a pharmaceutically acceptable prodrug, salt, solvate, or clathrate thereof than is generally required for systemic administration.

In one embodiment, the dosage is from about 0.0001 mg/kg to 1.0 mg/kg, more preferably from 0.0001 mg/kg to 0.5 mg/kg, more preferably from 0.001 mg/kg to 0.1 mg/kg, more preferably from 0.001 mg/kg to 0.01 mg/kg, more preferably from 0.0001 mg/kg to 0.003 mg/kg, more preferably from 0.0001 mg to 0.001 mg/kg.

In some embodiments, cerivastatin, an analog of cerivastatin, or a pharmaceutically acceptable prodrug, salt, solvate, or clathrate thereof is administered at dosage of less than 1 mg/kg per day, more preferably at a dosage of less than 0.1 mg/kg per day, most preferably at a dosage of less than 0.01 mg/kg per day. In certain embodiments, an analog of cerivastatin, or a pharmaceutically acceptable prodrug, salt, solvate, or clathrate thereof is administered at dosage of between 0.001 mg/kg per day and 0.0001 mg/kg per day. In some embodiments cerivastatin, an analog of cerivastatin, or a pharmaceutically acceptable prodrug, salt, solvate, or clathrate thereof is administered at dosage of less than 1 mg/kg per week, more preferably at a dosage of less than 0.3 mg/kg per week, most preferably at a dosage of less than 0.01 mg/kg per week. In certain embodiments, an analog of cerivastatin, or a pharmaceutically acceptable prodrug, salt, solvate, or clathrate thereof is administered at dosage of between 0.001 mg/kg per day and 0.0001 mg/kg per day.

The pharmaceutical formulation may be administered, for example, in a single dosage, as a continuous dosage, one or more times daily, or less frequently, such as once a week. In some cases, the pharmaceutical formulation is administered over a prolonged period of time to treat or prevent one or more symptoms of pulmonary arterial hypertension. The pharmaceutical formulations can be administered once a day or more than once a day, such as twice a day, three times a day, four times a day or more. The compositions can be administered for a period of at least one week, two weeks, three weeks, four weeks, one month, two months, three months, four months, five months, six months, seven months, eight months, nine months, ten months, eleven months, one year, or longer. In other embodiments, the pharmaceutical formulation is administered on a one-time basis (i.e., acute administration), for example, to a patient experiencing an acute pulmonary arterial hypertension event.

The effective dosage can be decreased by using targeted or selective delivery to the pulmonary system, for example, using a targeting peptide as described by Urakami, et al. Am. J. Pathol. 178(6):2489-2495 (2011).

In some cases, dosage forms useful for the administration a pharmaceutical formulation containing a therapeutically effective amount of cerivastatin, an analog of cerivastatin, or a pharmaceutically acceptable prodrug, salt, solvate, or clathrate thereof will be distributed in an administration kit. The kit may include one or a plurality of doses of a pharmaceutical formulation containing a therapeutically effective amount of cerivastatin, an analog of cerivastatin, or a pharmaceutically acceptable prodrug, salt, solvate, or clathrate thereof in combination with one or more devices for pulmonary administration of the formulation to a patient. In some cases, the kit can additionally contain a carrier or diluent (which is used, for example, to dissolve or suspend a solid formulation prior to delivery), a case, and instructions for employing the appropriate administration device.

In some cases, a pharmaceutical formulation containing cerivastatin, an analog of cerivastatin, or a pharmaceutically acceptable prodrug, salt, solvate, or clathrate thereof is administered to a patient in need thereof in a therapeutically effective amount to decrease the resting mean pulmonary artery pressure of a patient by at least 10%, more preferably at least 15%, most preferably at least 20%. In some embodiments, a pharmaceutical formulation containing cerivastatin, an analog of cerivastatin, or a pharmaceutically acceptable prodrug, salt, solvate, or clathrate thereof is administered to a patient in need thereof in a therapeutically effective amount to decrease the resting mean pulmonary artery pressure of a patient by greater than 20%, more preferably greater than 25%, most preferably greater than 30%.

In some cases, a pharmaceutical formulation containing cerivastatin, an analog of cerivastatin, or a pharmaceutically acceptable prodrug, salt, solvate, or clathrate thereof is administered to a patient in need thereof in a therapeutically effective amount to increase the pulmonary artery acceleration time in patient by at least 10%, more preferably at least 15%, most preferably at least 20%.

In some cases, a pharmaceutical formulation containing cerivastatin, an analog of cerivastatin, or a pharmaceutically acceptable prodrug, salt, solvate, or clathrate thereof is administered to a patient in need thereof in a therapeutically effective amount to decrease the pulmonary vascular resistance of a patient by at least 10%, more preferably at least 15%, most preferably at least 20%. In some embodiments, a pharmaceutical formulation containing cerivastatin, an analog of cerivastatin, or a pharmaceutically acceptable prodrug, salt, solvate, or clathrate thereof is administered to a patient in need thereof in a therapeutically effective amount to decrease the pulmonary vascular resistance of a patient by greater than 20%, more preferably greater than 25%, most preferably greater than 30%.

In patients suffering from PAH, pulmonary arterial obstruction by vascular proliferation and remodeling results in increased vascular resistance. Eventually, the increased workload placed on the heart causes right ventricular hypertrophy (i.e., a thickening of the right ventricular wall). In some cases, a pharmaceutical formulation containing cerivastatin, an analog of cerivastatin, or a pharmaceutically acceptable prodrug, salt, solvate, or clathrate thereof is administered to a patient in need thereof in a therapeutically effective amount to decrease the thickness of the patient's right ventricular wall by at least 10%, more preferably at least 15%, most preferably at least 20%.

As discussed above, elevated ADMA levels have been observed in patients suffering from PAR ADMA inhibits the activity of nitric oxide synthases in vivo, decreasing the amount of the vasodilator NO in a patient, and resulting in increased pulmonary vascular resistance. DDAH metabolizes ADMA in vivo, with DDAH2 representing the predominant endothelial DDAH isoform. Without wishing to be bound by theory, by selectively inducing DDAH2 activity in a patient, ADMA levels can be lowered, resulting in an increase in NO levels and a decrease in pulmonary vascular resistance.

In some embodiments, a pharmaceutical formulations containing cerivastatin, an analog of cerivastatin, or a pharmaceutically acceptable prodrug, salt, solvate, or clathrate thereof is administered to a patient in need thereof in a therapeutically effective amount to induce DDAH2 activity in a patient. In some cases, a pharmaceutical formulation containing cerivastatin, an analog of cerivastatin, or a pharmaceutically acceptable prodrug, salt, solvate, or clathrate thereof is administered in an amount effective to increase DDAH2 gene expression in cells by at least 30%, more preferably at least 100%, more preferably at least 400%, most preferably at least 500%.

Preferably, the pharmaceutical formulation is administered to a patient in need thereof in a therapeutically effective amount to selectively induce DDAH2 activity in a patient relative to DDAH1 activity. In certain embodiments, the pharmaceutical formulations contain an amount cerivastatin, an analog of cerivastatin, or a pharmaceutically acceptable prodrug, salt, solvate, or clathrate thereof is administered in an amount effective to increase DDAH2 gene expression in the endothelial cells of the pulmonary arteries of a patient by at least 30%, more preferably at least 100%, more preferably at least 400%, most preferably at least 500%.

As discussed above, chemokine receptors, such as CCR2, are known to play a role in the establishment and maintenance of a chronic inflammatory state in the pulmonary arteries of patients suffering from PAH. Studies have demonstrated that CCR2 overexpression in pulmonary cells represents another important underlying mechanism for the pulmonary vascular remodeling in PAH.

Preferably, the pharmaceutical formulation is administered to a patient in need thereof in a therapeutically effective amount to decrease CCR2 expression in lung/pulmonary artery. In certain embodiments, a pharmaceutical formulation containing cerivastatin, an analog of cerivastatin, or a pharmaceutically acceptable prodrug, salt, solvate, or clathrate thereof is administered in an amount effective to decrease CCR2 expression in lung/pulmonary artery by at least 15%, more preferably by at least 25%, most preferably by at least 50%.

Transcription factor Krueppel-like factor 2 (KLF2) is believed to control the expression of CCR2 in cells. By inducing expression of KLF2, it is believed that expression of CCR2 in cells can be reduced. Preferably, the pharmaceutical formulation is administered to a patient in need thereof in a therapeutically effective amount to increase KLF2 expression in pulmonary cells. In certain embodiments, a pharmaceutical formulation containing cerivastatin, an analog of cerivastatin, or a pharmaceutically acceptable prodrug, salt, solvate, or clathrate thereof is administered in an amount effective to increase KLF2 expression in lung/pulmonsry artery by at least 50%, more preferably by at least 100%, more preferably by at least 300%, most preferably by at least 500%.

D. Co-Administration

In some cases, pulmonary arterial hypertension is associated with one or more underlying risk factors, diseases, or disorders. In such cases, a pharmaceutical formulation containing a therapeutically effective amount of cerivastatin, an analog of cerivastatin, or a pharmaceutically acceptable prodrug, salt, solvate, or clathrate thereof can be co-administered with one or more therapeutic, diagnostic, or prophylactic agents to treat, diagnose or prevent a disease or disorder associated with PAH.

In some cases, a pharmaceutical formulation containing a therapeutically effective amount of cerivastatin, an analog of cerivastatin, or a pharmaceutically acceptable prodrug, salt, solvate, or clathrate thereof is administered to a patient in combination with one or more treatments for a collagen vascular disease (e.g., scleroderma, lupus erythematosus), a congenital systemic-to-pulmonary shunt (including simple, complex, and combined shunts which may be large or small, and may be corrected, partially corrected, or noncorrected), portal hypertension, HIV infection, drug use (e.g., cocaine, anorexigens), toxin exposure, a thyroid disorder, a glycogen storage disease, Gaucher's disease, hereditary hemorrhagic telangiectasia, a hemoglobinopathie (e.g., sickle cell disease), a myeloproliferative disorder, or a splenectomy.

In some cases, a pharmaceutical formulation containing a therapeutically effective amount of cerivastatin, an analog of cerivastatin, or a pharmaceutically acceptable prodrug, salt, solvate, or clathrate thereof is administered to a patient in combination with one or more treatments for COPD, asthma, interstitial lung disease, sleep-disordered breathing, an alveolar hypoventilation disorder, or a developmental abnormality.

In some cases, a pharmaceutical formulation containing a therapeutically effective amount of cerivastatin, an analog of cerivastatin, or a pharmaceutically acceptable prodrug, salt, solvate, or clathrate thereof is administered to a patient in combination with one or more treatments for thromboembolic obstruction or a non-thrombotic embolism.

The present invention will be further understood by reference to the following non-limiting examples.

EXAMPLE 1

Effect of Cerivastatin on DDAH2, DDAH1, KLF2 and CCR2 Levels

Materials and Methods

Human umbilical endothelial cells were seeded in 6-well plates (50,000 cells per well) and incubated with EGM (endothelial cell growth medium with bullet kit, Lonza) overnight. Then, triplicate wells were treated with indicated concentrations of cerivastatin in 2 ml of EGM. After 24 hours, total RNA was extracted using the RNeasy Kit (Qiagen, Valencia, Calif. After reverse transcription (RT) using the High Capacity cDNA Reverse Transcription Kit (Applied Biosystems, Foster City, Calif.), PCR was performed using an ABI Prism 7500 Sequence Detection System (Applied Biosystems, Foster City, Calif.) and QuantiTect SYBR Green PCR Master Mix (Qiagen, Valencia, Calif.). All reactions were carried out in triplicate, and each mRNA copy level was quantified using comparative CT method. Expression of actin was used as an endogenous control in all experiments and relative fold changes were calculated. All data were expressed as the means±standard deviation. The gene-specific forward and reverse primer sequences were 5'-gatgagattggcatggcttt-3'(SEQ ID NO: 2) and 5'-gtcaccttcac-cgttccagt-3' (SEQ ID NO: 3) for actin;

5'-ctgcccactcctgttgtttt-3' (SEQ ID NO: 4) and 5'-ggggtgt-tgaagcaat-3' (SEQ ID NO: 5) for DDAH-1;

5'-agctgctgactgcctctttc-3' (SEQ ID NO: 6) and 5'-ccagttct-gagcaggacaca-3' (SEQ ID NO: 7) for DDAH-2.

Effect of Statins on KLF2 and CCR2 Gene Expression:

THP-1 cells were obtained from the American Tissue Type Culture Collection (ATCC). Cells were maintained in RPMI-1640 (Mediatech, Manassas, Va.) containing 10% fetal bovine serum (FBS; Sigma-Aldrich) and 1% penicillin/streptomycin (Sigma-Aldrich), and incubated in a humidified incubator containing 5% $CO_2$/95% air at 37° C. In all experiments, cells were seeded at the concentration of $5 \times 10^5$ cells/mL in 12 well plates and then various statins were added to the medium. After 1 h, EPS at a final concentration of 100 ng/ml or TNF-□ at a final concentration of 10 ng/mL was added to the cultures. Cell pellets were collected for RNA and protein isolation.

Real-Time Reverse Transcription-PCR Analysis

Figure 1B:
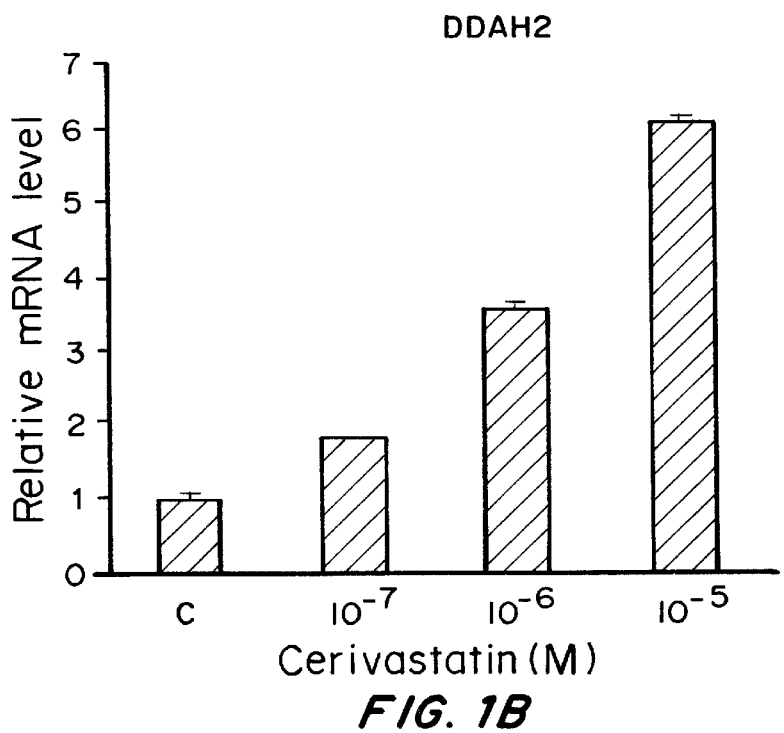

Total RNA was extracted using the RNeasy Kit (Qiagen, Valencia, Calif.) according to the manufacturer's instructions. After reverse transcription (RT) using the High Capacity cDNA Reverse Transcription Kit (Applied Biosystems, Foster City, Calif.), PCR was performed using an ABI Prism 7500 Sequence Detection System (Applied Biosystems, Foster City, Calif.) and QuantiTect SYBR Green PCR Master Mix (Qiagen, Valencia, Calif.). All reactions were carried out in triplicate, and each mRNA copy level was quantified using comparative CT method. Expression of actin was used as an endogenous control in all experiments and relative fold changes were calculated. All data were expressed as the means±standard deviation. Gene primer used for RT-PCR were 5'-cacgatcctccttgacgagt-3' (SEQ ID NO: 8) and 5'-tct-cacaaggcatcacaagc-3'(SEQ ID NO: 9) for CCR2 and KLF2 respectively, Results FIGS. 1A and 1B shows the effect of cerivastatin on the expression of DDAH1 (FIG. 1A) and DDAH2 (FIG. 1B) in endothelial cells. In both cases, the relative mRNA level is plotted as a function of cerivastatin concentration (mol/L). Cerivastatin selectively induces DDAH2 gene expression in human endothelial cells. FIG. 1A shows that cerivastatin has a relatively small and non-concentration dependent effect on the expression of DDAH1 in endothelial cells, while FIG. 1B shows that cerivastatin has a significant (more than 600%) and dose dependent effect on the expression of DDAH2.

Figure 2A:
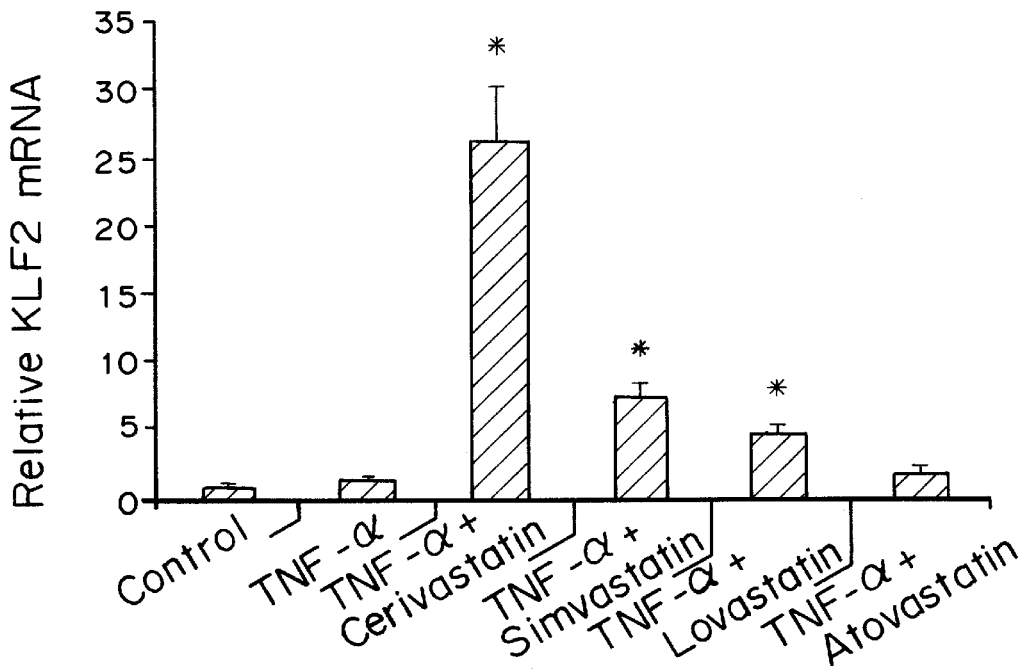
FIGS. 2A and 2B show the effect of cerivastatin compared with three other statins, the HMG-CoA reductase inhibitors simvastatin, lovastatin, and atovastatin, on the expression of KLF2 (FIG. 2A) and CCR2 (FIG. 2B) in human THP-1 cells.
Figure 2B:
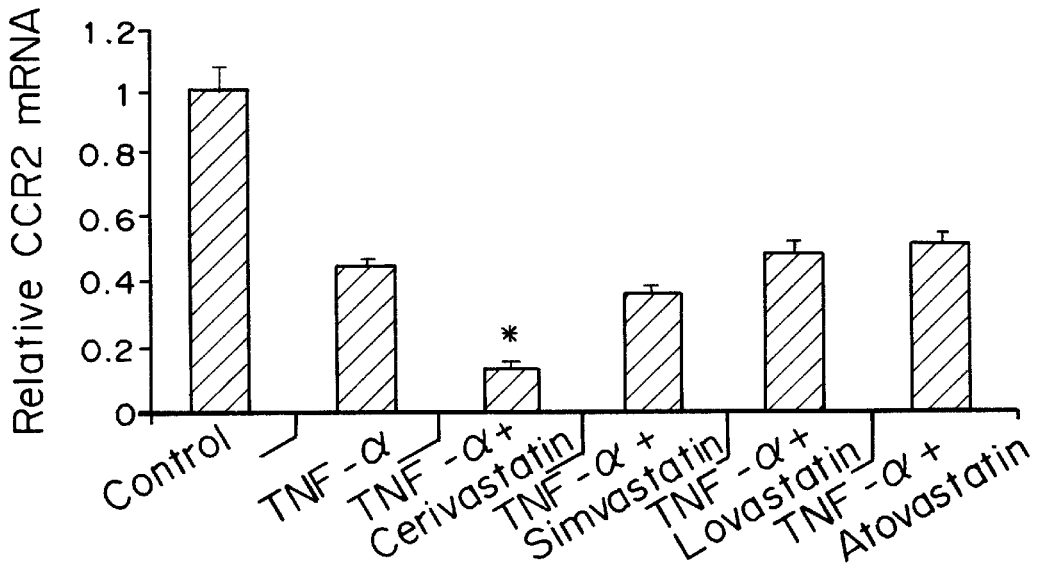

FIGS. 2A and 2B show the effect of cerivastatin compared with three other statins, the HMG-CoA reductase inhibitors simvastatin, lovastatin, and atovastatin, on the expression of KLF2 (FIG. 2A) and CCR2 (FIG. 2B) in human THP-1 cells. FIGS. 2A and 2B plot the relative KLF2 and CCR2 mRNA levels upon administration of tumor necrosis factor alpha (TNF-α), TNF-α+10 μM cerivastatin, TNF-α+10 μM simvastatin, TNF-α+10 μM lovastatin, TNF-α+10 μM atorvastatin.

EXAMPLE 2

Demonstration of Efficacy in Rat Model

Abbreviations
Pulmonary Artery Hypertension (PAH)
Monocrotaline (MCT)
Intratracheal (I.T.)
Pulmonary Artery (PA)
Right Ventricle (RV)
PA acceleration time (PAAT)
inerventricular septum (IVS)
  Materials and Methods
  Animal Protocol
The Saint Joseph's Research Institute is accredited by the Association for Accreditation and Advancement of Laboratory Animal Care. Experiment animal use conformed to National Institute of Health and American Heart Association guidelines and was approved by the Institutional Animal Care and Use Committee of the Saint Joseph's Research Institute, in accordance with the "Guide for the Care and Use of Laboratory Animals" (NIH publication no. 85-23, National Academy Press, Washington, D.C., revised 1996).

PAH was induced in adult male Sprague-Dawley rats (~375 to 425 g, n=12, Harlan Laboratories) by a single, subcutaneous injection of monocrotnil (MCT) (60 mg/kg; n=24). Schultze, A. E. and Roth, R. A. J. Toxicol. Environ. Health. B, Crit. Rev. 1(4): 271-346 (1998). The animals injected with MCT were randomly assigned to 2 groups that received intratracheal (I.T.) aerosol instillation (MicroSprayer® Aerosolizer Model IA-1B, PennCentury, Inc.) of PBS twice weekly (200 μl; n=6), and a second group received IT. aerosol instillation of Cerivastatin twice weekly (2 mg/ml in PBS; n=6 I.T. instillations of PBS and Cerivastatin were administered the day of MCT injection until the rats were euthanized on day 42.

Echocardiography was performed at day 14, 28, and 42. Right heart catheterization was performed on day 42 before being euthanized. Sedation was induced by placing the rat in an anesthesia induction chamber with gas flow at 1 l/min, and the isoflurane was delivered via vaporizer at 3-4%. After induction, the rat was intubated and remained anesthetized with inhalant isoflurane at 1% for echo and 2% for right heart catheterization.

Echocardiography
After shaving the chest, 70% isopropyl alcohol was applied as the ultrasound transmission media and transthoracic echocardiography was performed (GE vivid i with i12L-RS linear array transducer, 5.0-13.0 MHz). The 2-D modality was applied to measure PA diameter at the level of the pulmonary outflow tract from the parasternal short-axis view. PA acceleration time (PAAT) and PA flow velocity time integral (VTI) were measured using pulse-wave Doppler with the sample volume centrally positioned in the PA distal to the pulmonary valve. Angle correction was used to adjust the pulse-wave cursor such that it was positioned parallel to pulmonary artery flow. By combining PA VTI with the PA cross-sectional area, echocardiographically derived stroke volume was determined. M-mode was applied to measure right ventricular cavity thickness during end diastole using the parasternal long-axis view obtained from the right side of the rat.

Invasive PA Pressure Measurements by Right Heart Catheterization

A 1.4-F micromanometer-tipped Millar pressure catheter (Millar Instruments) was used to measure systolic (sPAP), mean (mPAP), and diastolic PA pressure (dPAP) in all rats. The Millar pressure catheter was connected to a Digi-Med Blood Pressure Analyzer (Micro-Med, Inc., Louisville, Ky.) and viewed using Digi-Med System Integrator software. With fluoroscopy guidance (GE OEC 9800 C-arm) a 18 G intravenous (I.V.) catheter (Terumo Surflo®) was punctured though the closed chest of the animal and into the right ventricular cavity. 200 units/kg of heprin was then given through the I.V. catheter to prevent thrombosis. A modified Surflo® injection plug was then placed on the end of the I.V. catheter to prevent the animal from bleeding out. The 1.4-F Millar pressure catheter was then fed through the modified injection plug through the I.V. catheter and into the RV outflow tract. It was then advanced through the pulmonary valve and up into the PA confirmed by fluoroscopy and pressure wave-form.

Tissue and Blood Collection/Analysis

After recording hemodynamic measurements and collecting blood, the animals were euthanized under deep anesthesia (isoflurane 5%) and the lungs and heart were isolated. The RV free wall was dissected from the left ventricle and interventricular septum (IVS), and the wet weight of each was recorded. RV hypertrophy was obtained as a RV weight/(LV+IVS weights) ratio.

PA was carefully isolated and fixed in 10% neutral buffered formalin, embedded in paraffin, then processed (6- to 8-μm thick sections) for histomorphometry measurements of media-to-lumen ratio. The left lung was inflated with and placed in 10% neutral buffered formalin. The tissue specimens were then processed, embedded in paraffin and sectioned (6- to 8-μm thick) for histopathology analysis.

Results

Figure 3:
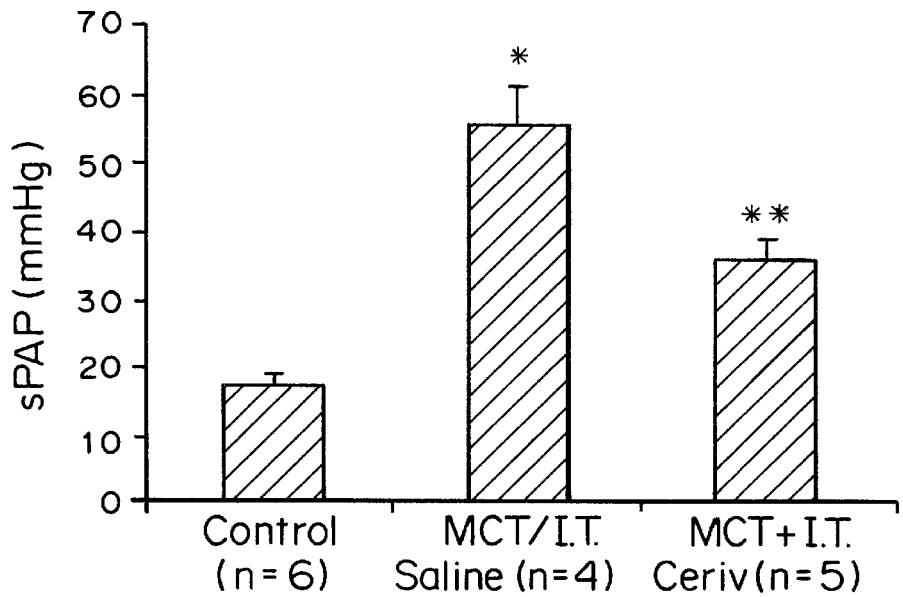
FIG. 3 is a graph demonstrating the ability of cerivastatin to decrease systolic pulmonary artery pressure (sPAP, mm Hg) in a rat model of PAH. sPAP was measured using right heart catheterization as described in Example 1. Injection of MCT (simulating PAH) increases sPAP. Intratracheal injection of cerivastatin resulted in a statistically significant decrease in sPAP relative to the MCT injection PAH model.

FIG. 3 is a graph of sPAP) demonstrating the ability of cerivastatin to decrease systolic pulmonary artery pressure (sPAP, mm Hg) in a rat model of PAH. sPAP was measured using right heart catheterization as described in Example 1. Injection of MCT (simulating PAH) increases sPAP. Intratracheal injection of cerivastatin resulted in a statistically significant decrease in sPAP relative to the MCT injection PAH model.

Figure 4:
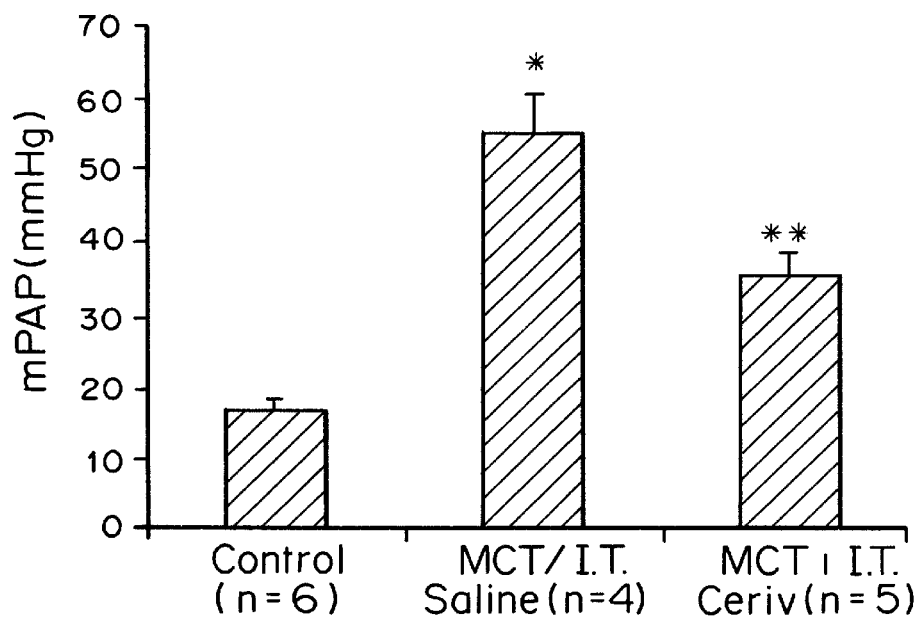
FIG. 4 is a graph of percent change relative to control of mPAP, demonstrating the ability of cerivastatin to decrease mean pulmonary artery pressure (mPAP, mm Hg) in a rat model of PAH. mPAP was measured using right heart catheterization as described in Example 1. Injection of MCT (simulating PAH) resulted an increase in mPAP. Intratracheal injection of cerivastatin resulted in a statistically significant decrease in mPAP relative to the MCT injection PAH model.

FIG. 4 is a graph of percent change relative to control of mPAP demonstrating the ability of cerivastatin to decrease mean pulmonary artery pressure (mPAP, mm Hg) in a rat model of PAH. mPAP was measured using right heart catheterization as described in Example 1, Injection of MCT (simulating PAH) resulted an increase in mPAP. Intratracheal injection of cerivastatin resulted in a statistically significant decrease in mPAP relative to the MCT injection PAH model.

Figure 5A:
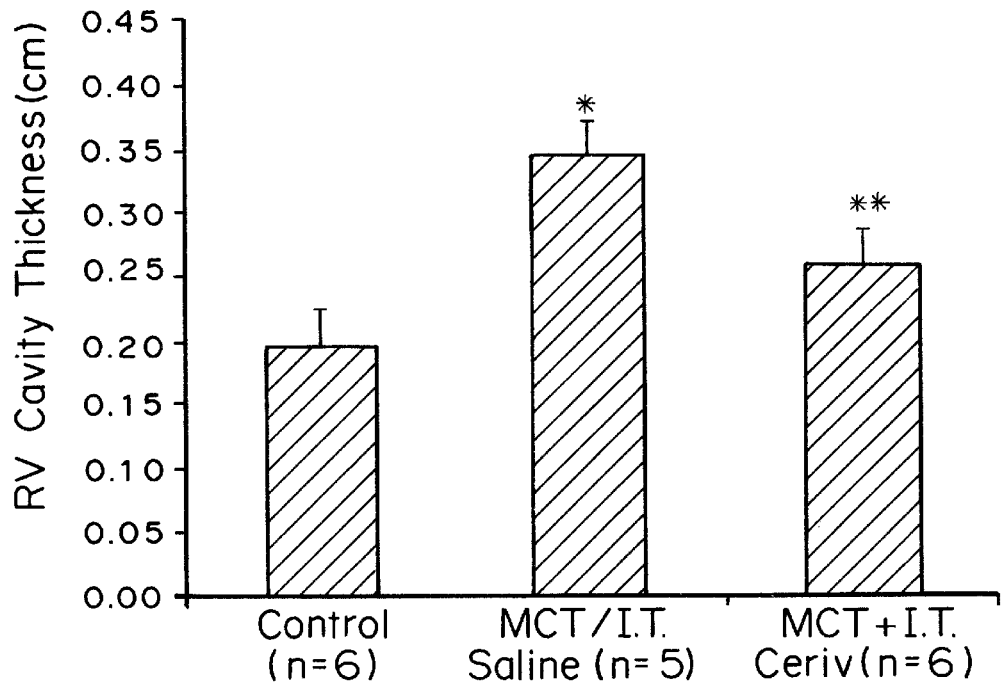
FIGS. 5A and 5B demonstrate that intratracheal injection of cerivastatin significantly reduced right ventricle (RV) cavity thickening relative to the MCT injection PAH model.
Figure 5B:
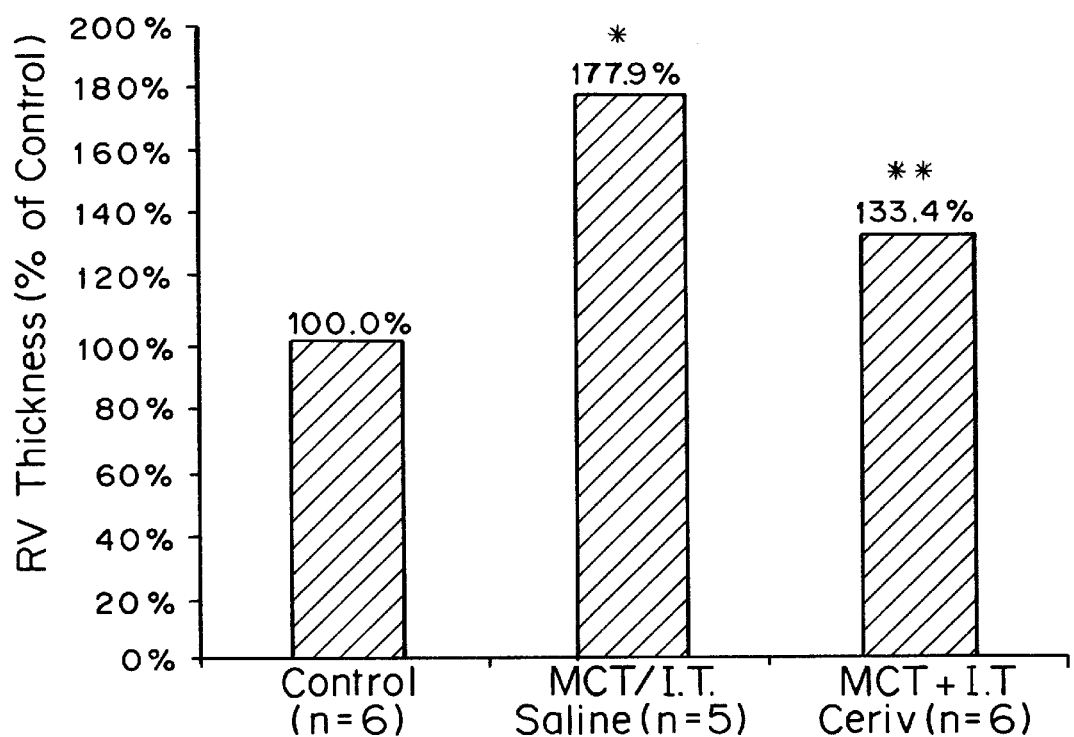

FIGS. 5A and 5B demonstrate that intratracheal injection of cerivasatin significantly reduced mean right ventricle thickening relative to the MCT injection PAH model. FIG. 5A is RV cavity thickness (cm). FIG. 5B is RV thickness as percent of control.

Figure 6:
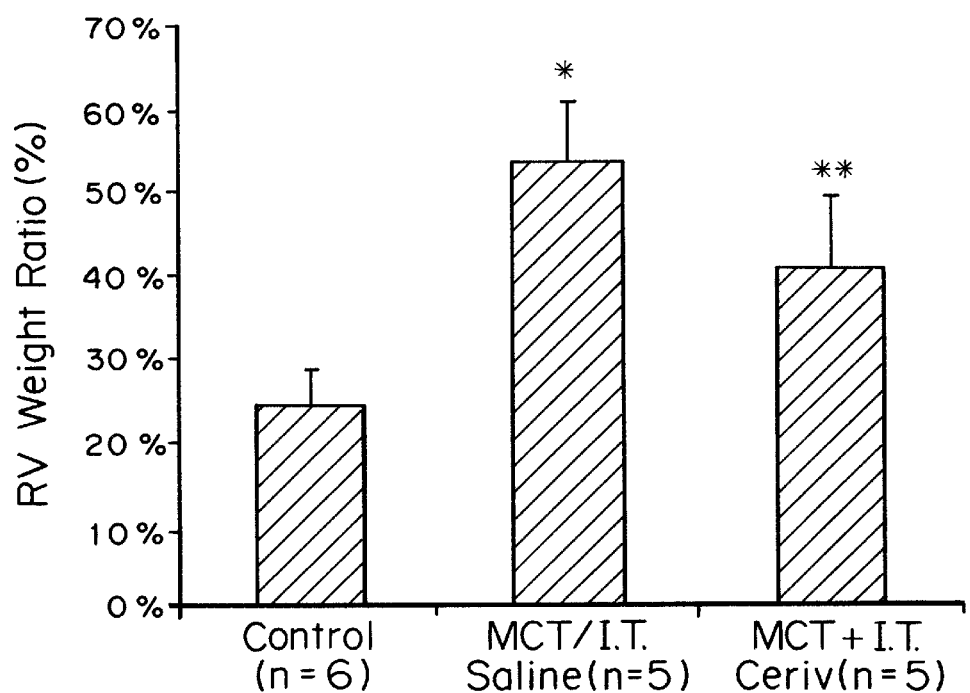
FIG. 6 is a graph demonstrating that intratracheal administration of cerivastatin significantly reduces right ventricular (RV) weight ratio in a rat model of PAH. The RV weight ratio (weight of the right ventricle/(weight of the left ventricle+ weight of the septum), plotted as a percent increased upon injection of MCT (simulating PAH). Intratracheal injection of cerivastatin significantly reduced RV weight ratio relative to the MCT injection PAH model.

FIG. 6 is a graph demonstrating that intratracheal administration of cerivastatin significantly reduces right ventricular (RV) weight ratio in a rat model of PAH. The RV weight ratio (weight of the right ventricle/(weight of the left ventricle+ weight of the septum), plotted as a percent increased upon injection of MCT (simulating PAH). Intratracheal injection of cerivastatin significantly reduced RV weight ratio relative to the MCT injection PAH model.

Figure 7A:
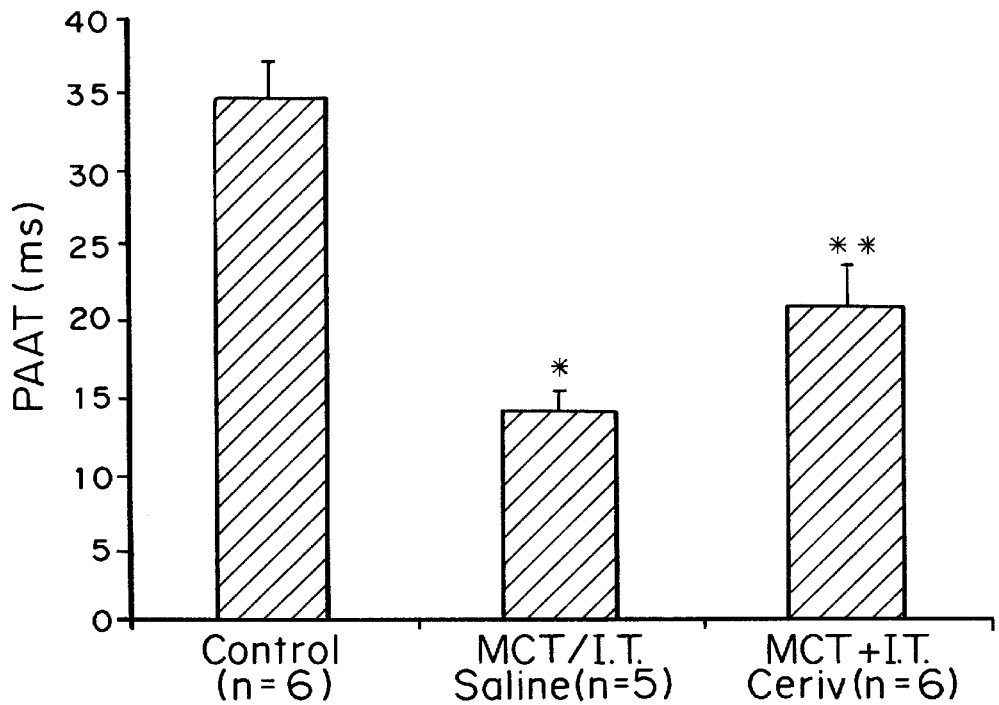
FIGS. 7A and 7B are graphs plotting the pulmonary artery acceleration time (PAAT) in a rat model of pulmonary arterial hypertension. PAAT was measured using echocardiography as described in Example 1. Injection of MCT (simulating PAH) resulted in a decrease in PAAT (FIG. 7A, expressed as ms). Intratracheal cerivastatin significantly increased PAAT.
Figure 7B:
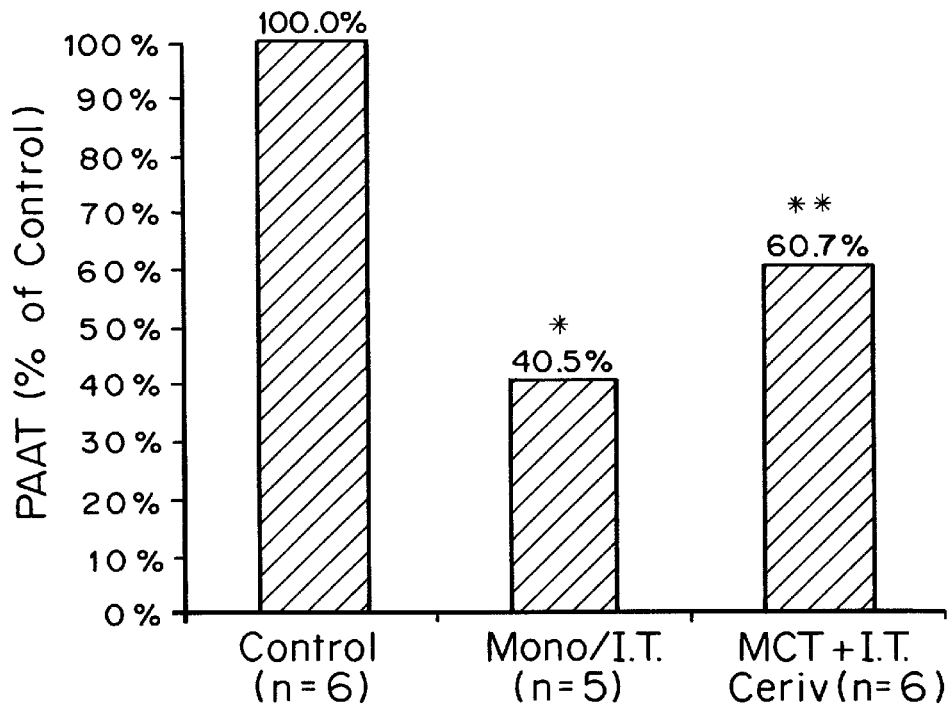

FIGS. 7A and 7B are graphs plotting the pulmonary artery acceleration time (PAAT) in a rat model of pulmonary arterial hypertension. PAAT was measured using echocardiography as described in Example 1. Injection of MCT (simulating PAH) resulted in a decrease in PAAT (FIG. 7A, expressed as ms). Intratracheal cerivastatin significantly increased PAAT. FIG. 7B shows that injection of MCT (simulating PAH) resulted in a decrease in PAAT to 40.5% of the control. Intratracheal injection of cerivastatin resulted in a statistically significant increase in PAAT to 60.7% of the control.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method of treating pulmonary arterial hypertension (PAH), comprising administering to a patient in need thereof via pulmonary administration a pharmaceutical formulation consisting of an active agent and one or more pharmaceutically acceptable carriers, excipients, or additives, wherein the active agent is cerivastatin, a cerivastatin analog, or a pharmaceutically acceptable salt, clathrate, or solvate thereof and a pharmaceutically acceptable carrier.

2. The method of claim 1, wherein the pharmaceutical formulation is an aerosol.

3. The method of claim 2, wherein the aerosol comprises liquid particles suspended in a gas.

4. The method of claim 1 wherein the active agent is incorporated into a polyketal polymer to form an active agent-polyketal polymer particle.

5. The method of claim 1, wherein the cerivastatin, cerivastatin analog, or pharmaceutically acceptable salt, clathrate, or solvate or pharmaceutically acceptable carrier thereof is conjugated with the cyclic peptide, CARSKNKDC (SEQ ID NO: 1).

6. The method of claim 4, wherein the particle has a tap density less than about 0.4 g/cm$^3$ or a mass median aerodynamic diameter (MMAD) of between about 0.5 and about 5.0 microns.

7. The method of claim 1, wherein the pharmaceutical formulation is administered using a nebulizer, dry powder inhaler, or pressurized metered dose inhaler.

8. The method of claim 1, wherein the pharmaceutical formulation is administered at dosage of less than 1 mg/kg per day.

9. The method of claim 8, wherein the pharmaceutical formulation is administered at a dosage of less than 0.01 mg/kg per day.

10. The method of claim 1, wherein the pharmaceutical formulation is administered daily.

11. The method of claim 1, wherein the pharmaceutical formulation is administered less frequently than daily.

12. The method of claim 1, wherein the formulation is administered in an effective amount to induce DDAH2 gene expression in the patient.

13. The method of claim 1, wherein the formulation is administered in an effective amount to decrease CCR2 gene expression and inflammation in the patient.

14. The method of claim 13, wherein CCR2 gene expression in the patient is decreased by at least 15%.

15. The method of claim 1, wherein the pulmonary arterial hypertension is idiopathic pulmonary arterial hypertension (IPAH) or familial pulmonary arterial hypertension (FPAH).

16. The method of claim 1, wherein the pulmonary arterial hypertension is associated with a disease or disorder selected from the group consisting of collagen vascular diseases, congenital systemic-to-pulmonary shunts, portal hypertension, HIV infection, drug use, toxin exposure, thyroid disorders, glycogen storage diseases, Gaucher's disease, hereditary hemorrhagic telangiectasia, hemoglobinopathies, myeloproliferative disorders, chronic obstructive pulmonary disease (COPD), asthma, interstitial lung disease, sleep-disordered breathing, alveolar hypoventilation disorders, developmental abnormalities, a splenectomy, and combinations thereof.

17. A formulation for pulmonary administration consisting of an active agent and one or more pharmaceutically acceptable carriers, excipients, or additives, wherein the active agent is cerivastatin, a cerivastatin analog, or a pharmaceutically acceptable salt, clathrate, or solvate thereof.

18. The method of claim 1, wherein the active agent of the pharmaceutical formulation is in the form of a (i) a dry powder comprising solid particles or (ii) an aqueous solution.

19. The pulmonary formulation of claim 17, wherein the active agent is in the form of (i) a dry powder comprising solid particles or (ii) an aqueous solution.

* * * * *

SEQUENCE LISTING

```
<160> NUMBER OF SEQ ID NOS: 9

<210> SEQ ID NO 1
<211> LENGTH: 9
<212> TYPE: PRT
<213> ORGANISM: Artificial Sequence
<220> FEATURE:
<223> OTHER INFORMATION: Synthetic cyclic peptide
<220> FEATURE:
<221> NAME/KEY: MISC_FEATURE
<222> LOCATION: (1)..(9)
<223> OTHER INFORMATION: Cyclic

<400> SEQUENCE: 1

Cys Ala Arg Ser Lys Asn Lys Asp Cys
1               5

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
gatgagattg gcatggcttt                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
gtcaccttca ccgttccagt                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
ctgcccactc ctgttgtttt                                                  20
```

```
<210> SEQ ID NO 5
<211> LENGTH: 16
<212> TYPE: DNA
<213> ORGANISM: Artificial Sequence
<220> FEATURE:
<223> OTHER INFORMATION: Synthetic primer

<400> SEQUENCE: 5 gggtgttga agcaat                                                     16

<210> SEQ ID NO 6
<211> LENGTH: 20
<212> TYPE: DNA
<213> ORGANISM: Artificial Sequence
<220> FEATURE:
<223> OTHER INFORMATION: Syntheitc primer

<400> SEQUENCE: 6
agctgctgac tgcctctttc                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
ccagttctga gcaggacaca                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
cacgatcctc cttgacgagt                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
tctcacaagg catcacaagc                                                20
```